(12) United States Patent
Chang

(10) Patent No.: US 8,344,115 B2
(45) Date of Patent: Jan. 1, 2013

(54) IMMUNOASSAY FOR SPECIFIC DETERMINATION OF S-ADENOSYLMETHIONINE AND ANALOGS THEREOF IN BIOLOGICAL SAMPLES

(76) Inventor: Chiu Chin Chang, Sunnyvale, CA (US); Chan-Sui Pang, legal representative, Sunnyvale, CA (US)

( * ) Notice: Subject to any disclaimer, the term of this patent is extended or adjusted under 35 U.S.C. 154(b) by 425 days.

(21) Appl. No.: 12/385,749

(22) Filed: Apr. 17, 2009

(65) Prior Publication Data

US 2009/0263879 A1 Oct. 22, 2009

Related U.S. Application Data

(60) Provisional application No. 61/071,297, filed on Apr. 21, 2008.

(51) Int. Cl.
*C07K 16/00* (2006.01)
*G01N 33/532* (2006.01)

(52) U.S. Cl. ............... 530/389.8; 530/388.9; 530/391.3; 436/544

(58) Field of Classification Search ........................ None
See application file for complete search history.

(56) References Cited

U.S. PATENT DOCUMENTS

2003/0073149 A1* 4/2003 Archer et al. ................ 435/7.92
2007/0280946 A1* 12/2007 Numata et al. ............. 424/146.1

OTHER PUBLICATIONS

A rapid immunoassay for S-adenosylhomocysteine in plasma. Journal of Nutritional Biochemistry 2007, vol. 18, pp. 827-831.*
S-adenosylmethionine levels in the diagnosis of pneumocystis carinii pneumonia in patients with HIV infection. Clin. Infect. Dis. 2008, vol. 46, No. 3, pp. 467-471.*
Antibodies against the antibiotics: an overview. Ann. Ist. Super. Sanita. 1991, vol. 27, No. 1, pp. 149-154.*
Strategies for immunoassay hapten design. ACS Symposium Series 1995, vol. 586, Chapter 9, pp. 119-139.*

* cited by examiner

*Primary Examiner* — Shafiqul Haq
(74) *Attorney, Agent, or Firm* — Isaac A. Angres

(57) ABSTRACT

This invention pertains to a method for detecting a compound in the presence of other compounds that are substantially similar in structure and metabolically related to the analyte. The invention is particularly suited for the detection of S-adenosylmethionine in the presence of S-adenosylhomocysteine, other nucleosides and derivatives in a biological sample. The methods of this invention involve an antibody produced specifically against S-adenosylmethionine; particularly, analogs modified strategically at the sulfonium position. An assay protocol comprises chemically modified analyte analog linked to an enzymatic reporter and the aforementioned antibody was used to demonstrate the assay specificity and sensitivity. Additional assay method with immobilized immunogen, the specific antibody, and an enzyme labeled secondary antibody was also described for illustration. The invention also features hapten design and novel compounds used as haptens to prepare immunogen and for the specific antibody production.

16 Claims, 3 Drawing Sheets

IMMUNOASSAY FOR SPECIFIC DETERMINATION OF S-ADENOSYLMETHIONINE AND ANALOGS THEREOF IN BIOLOGICAL SAMPLES

This application claims the priority benefit under 35 U.S.C. section 119 of U.S. Provisional Patent Application No. 61/071,297 entitled "Immunoassay For Specific Determination Of S-Adenosylmethionine In Biological Samples", filed Apr. 21, 2008, which is in its entirety herein incorporated by reference.

FIELD OF THE INVENTION

This invention relates to clinical chemistry, particularly immunoassays. The present invention also relates to haptens. More specifically this invention relates to a method of determination of S-adenosylmethionine which has the benefit of high specificity to reagents used in such a method and to their preparation, and to kits useful in such a method. The present invention is further directed to reagents and methods for performing an immunoassay, to determine the presence and/or amount of S-adenosylmethionine in samples, particularly aqueous, fluid biological samples such as urine, whole blood, serum or plasma, cerebral spinal fluid (CSF), or saliva, to a method of making the reagents, and to an immunoassay based on the reagents. More particularly the invention is directed to new haptens, immunogens prepared from the haptens, antibodies raised against the immunogens containing the haptens and immunoassays which utilize reagents and methods of the invention.

This invention is also in the field of ligand receptor assays, including immunoassays, for the detection of S-adenosylmethionine in a biological sample such as urine, whole blood, CSF, serum or plasma, saliva, or cells, tissues, or organelles. More particularly, this invention relates to methods for the synthesis of novel hapten derivatives related to S-adenosylmethionine and protein and polypeptide derivative conjugates and labels for use in the preparation of antibodies to S-adenosylmethionine and S-adenosylmethionine analogs and for use in the immunoassay process.

More specifically, the invention relates to a system of analogs, conjugates and specific antibodies that can be used in assay systems for specific detection or quantitation of S-adenosylmethionine (SAM) and in the presence of structurally similar and metabolically related compounds such as S-adenosylhomocysteine (SAH) and adenosine, etc. in the sample.

The invention further features a method for determining the methylation index (ratio of concentration of SAM/concentration of SAH) in biological fluids.

The present invention also relates to S-adenosylmethionine and its analogs for use as immunodiagnostic reagents and in immunodiagnostic protocols. The present invention further relates to a method and kit for detecting or quantitating S-adenosylmethionine in a sample.

BACKGROUND OF THE INVENTION

The clinical diagnostic field has seen a broad expansion in recent years, both as to the variety of materials of interest that may be readily and accurately determined, as well as the methods for the determination. Over the last several decades, testing for numerous substances such as drugs of abuse, or other biological molecules of interest has become commonplace. In recent years, immunoassay based on the interaction of an antibody with an antigen has been extensively investigated for this purpose.

Based on the unique specificity and high affinity of antibodies, an immunoassay can accurately and precisely quantitate substances at the very low concentrations found in biological fluids. Immunoassay can be categorized according to its design. If the bound (to antibody) and the unbound antigens (or analytes) are not physically separated during the assay, it is called a homogeneous assay; otherwise, a heterogeneous assay. Immunoassays can use either labeled antigen or label antibody. The assay can be a competition assay (frequently used in small molecule detection; typically limited reagents are used), or a sandwich assay (for large molecules such as proteins; usually excess reagents are used). Depending on the signal generation and detection system utilized, immunoassay can be a turbidity or a nephelometry assay, a radioimmunoassay, a calorimetric assay, a fluorescence assay, a chemiluminescence assay, an enzyme-labeled assay (the signal may be measured by colorimetry, fluorometry, chemiluminescence, or bioluminescence, etc.), an electrogenerated chemiluminescent assay (ElectroChemical Luminescence or ECL assay), a target amplification assay (using methods such as PCR to amplify the target), or a signal amplification assay (via enzyme channeling or use liposome carrying a bag of signal, for example), etc.

By way of further background, a hapten may be defined as a chemical composition of limited molecular weight (usually less than 1000) which in and of itself does not elicit antibody formation when introduced into a host animal. However, when covalently bonded to a high molecular weight antigenic carrier, the resultant hapten-carrier conjugate can elicit in the host animal the formation of antibodies which recognize the hapten composition. Examples of haptens to which antibodies have been raised in this fashion are numerous, including such classes of materials as medicaments (therapeutic drugs), drugs of abuse, amino acids, dietary supplements, and metabolites, small peptides, steroids, hormones (such as thyroxine), and aromatic residues such as the dinitrophenyl moiety. Typical carriers are large polyvalent molecules such as proteins, polysaccharides and glycoproteins which are not native to the host animal. The methods for preparation of hapten-carrier conjugates are well known in the art and have been reviewed (B. F. Erlanger, Methods in Enzymology, v. 70, p. 84, 1980).

S-adenosyl methionine, commonly known as SAM, or SAM-e, or AdoMet, is a natural compound found in all living cells. It is one of the most used enzymatic substrates in biochemical reactions, second only to the universal energy storage and transfer molecule, adenosyl triphosphate (ATP).

The chemical structure of SAM is:

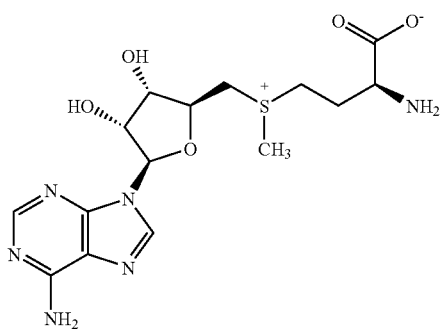

SAM plays a crucial role in the process called transmethylation. Methylation is involved in nearly every aspect of life. SAM is the primary "methyl" donor for a variety of methyl-transfer reactions in DNA, RNA, proteins, lipids, and small molecules in the body.

Proper DNA methylation is essential for normal embryonic development. Methyl-transferase gene homozygously deleted (knocked out) has been proven lethal (Pegg, A. E., Feith, D. J., Fong, L. Y., Coleman, C. S., O'Brian, T. G., and Shantz, L. M., 2003, Biochem. Soc. Trans. 31, 356-360). DNA improperly methylated has been found in many tumors. Alterations in DNA methylation patterns induce the expression of oncogenes or silence the expression of tumor suppressor genes, and methyl deficient diets have been shown to promote liver cancer in rodents. Methylation of DNA results in protection of the genome from restriction enzymes (Loenen, W. A. M., 2003, Nucleic Acids Res., 31, 7059-7069; Murray, N. E., 2000, Microbiol Mol Biol Rev, 64, 412-434). SAM has been shown to control gene expression by binding to structural domains embedded within the non-coding region of certain mRNAs (Corbino, K. A., Barrick, J. E., Lim, J., Tucker, B. J., Pusharz, I., Mandal, M., Rudnick, N. D., and Breaker, R. R., 2005, Genome Biol., 6, R70).

SAM provides the methyl group in the production of essential bio-molecules such as carnitine (the fat burner), acetyl-L-carnitine (the neuronutrient and membrane transporting agent), phosphocreatine (the primary ATP reservoir), epinephrine/adrenalin (the endogenous catecholamine, stress hormone and neurotransmitter), phosphatidylcholine (the most important membrane phospholipids), and melatonin (circadian rhythm modulator), etc.

In addition to transmethylation, SAM also plays a myriad of roles in other metabolic pathways. The transsulfuration begins with S-adenosylhomocysteine (SAH), the residual structure of SAM upon donating the methyl group (transmethylation). Hydrolysis of SAH yields homocysteine, which in turns converts to cystathionine, then cysteine, and eventually, to glutathione, the hepatocellular antioxidant and life-saving detoxification agent. Since dietary cysteine content is low, and up to 80% of dietary cysteine may lose its sulfhydryl groups through gastrointestinal tract, SAM is the main providing source of cysteine, the building block of glutathione.

The aminopropylation is another process initiated with SAM through decarboxylation. The decarboxylated SAM then couples with putrescine to generate spermidine and spermine which are critical to cell growth, differentiation and the stability of DNA and RNA. Furthermore, Methylthioadenosine (MTA), the by-product of polyamine synthesis, is a powerful analgesic and anti-inflammatory agent. This may be, at least partially, responsible for the clinical benefits observed in the treatment of osteoarthritis, rheumatoid arthritis and fibromyalgia with SAM (G. Stamentinoli, 1987, Pharmacologic aspects of SMe, Am J Med, 83 (suppl 5A), 35-42; C. di Padova, 1987, SAMe in the treatment of osteoarthritis, Am J Med 83 (supp 5A), 60-65; A. Tavoni et al, 1987, evaluation of SAMe in Primary Fibromyalgia, Am J Med, 83 (suppl 5A), 107-110).

More recently, it has been recognized that SAM, in the presence of Vitamin $B_{12}$, gives rise to 5'-deoxyadenosyl radical which generates other radicals on the enzyme methionine synthetase or coupled enzymes (Toohey, J. I., Biofactors, 2006, 26(1) 45-57; Kozbial, P. S. and Mushegian, A. R., 2005, BMC Struct Biol, 5, 19.) The free radical propagation results in rearrangement or removal of toxic substances accumulated. One example is conversion of homocysteine to iso- or β-methionine, which is readily degraded to methanethiol.

Poor methylation or deficiency of SAM has been implicated or related to the development of birth defects, cardiovascular disease, cancer, liver disease, neurological dysfunction, mood swing, herpes outbreak, diabetes, depression, indigestion, chronic fatigue, and age-related illness such as Alzheimer's disease, etc.

Treatment with SAM has been proven to be as effective as prescription tricyclic antidepressants, non-steroidal anti-inflammatory drugs (NSAIDS), and showed efficacy in treatment of some liver conditions such as cholestasis of pregnancy and intrahepatic cholestasis associated with liver diseases (Healthcare Research and Quality, Dept of Health and Human Services). More significantly, SAM is well tolerated and no serious side effects have been noted. This is in contrast to those frequently associated with prescription antidepressants (e.g., headaches, weight gain, and sexual dysfunction, etc.) or NSAIDS (e.g., irritation and damage of gastrointestinal linings, even internal bleeding upon chronic use, and increase risk of heart disease). It also provides rapid onset of relief in comparison to the tricyclic antidepressant treatment. Additional benefits and claims have been published in both scientific literature and popular reporting, although further studies and confirmation were awaited. Usage of SAM by patient who suffers from bipolar disease is contraindicated for risks of exacerbation into manic depression.

It has been reported that SAM in the tissues of older rats is significantly lower that of the younger animals. Similar findings were reported in human with aging, dementia; liver disease, alcoholism, and depression (R. Baldessarini, 1997, Neuropharmacology of SAMe, Am J Med 83 (suppl 5A), 95-103) The importance of S-adenosylmethionine as a biomarker is without question. It may well be a vital link between health and disease, from birth to mature to prime and then to age.

In Europe SAM has been classified and sold as a drug (as Ademetionine) for treatment of depression, liver disorders, osteoarthritis and fibromyalgia since 1979 in Italy, since 1985 in Spain, and since 1989 in Germany (Teodoro Bottiglieri, Am J Clin Nutr 2002, 76 (suppl) 1151s-1157s.) In the United States, SAM is marketed as a dietary supplement for the comfort of bone and joint, support of liver health, and well being of mood since 1999. It has quickly become one of the most popular dietary supplements sold among the estimated 30,000 dietary items in the market. The regulation on dietary supplement is substantially less in comparison to drugs or pharmaceuticals. In view of being the primary methylating agent capable of modifying DNA, RNA, protein, and many functional molecules in the body it is critically important that scientific information is accurately documented and accessible. Guidelines and oversight on its use are in place. However, despite of the so far publicized safety record, clinical trials of SAM are mostly short-term studies, and generally involved only small number of patients. Information regarding to drug or food interactions with SAM is extremely limited.

Furthermore, neither the normal range of SAM concentration in blood/serum/plasma nor the optimal concentration had been extensively discerned and determined. Due to various reasons including patient population, sample handling, pretreatment, and detection methods, etc., published results were vastly inconsistent. Even from the same laboratory, utilizing similar technique, wide ranges of concentration have been reported for healthy patients. The data are in general most useful for comparison within the context of the particular studies.

Since SAM is an intrinsically unstable molecule, and its optical density maximum of 258-260 nm is not a distinguished absorption, the determination of its concentration in various biological fluids and tissues has always been a challenging task. A simple, convenient method that does not require costly instrumentation (LC, MS, and combinations) is clearly desirable for the determination of the biological concentration of SAM, and to monitor its change and metabolic paths in the body fluids, tissues and organelles. It is also critically necessary to understand the impact and consequence when SAM is been used daily as a nutritional supplement today.

The SAM concentration in the blood, serum or plasma of a healthy adult (or any age group) has not been established despite the fact that there have been substantial efforts and interests in determining the concentrations in various tissues or biological fluids, and in different health and disease conditions. Largely due to the absence of a reference standard for SAM itself, and the lack of an effective method to measure SAM from a biological sample, almost all studies utilize internal standard and the reported concentrations between studies varies greatly for healthy individuals as well as those in disease state.

The majority of SAM in blood is found in erythrocytes, with concentration at μM level (typically between 2 to 4 μM). Its concentration in serum or plasma for healthy adults is reported in the neighborhood of 60-150 nM. Variations in concentrations in these ranges continued to be reported from time to time perhaps due to problems such as instability of SAM, the lack of standardization of SAM and the sample handling issues. The concentration in CSF appears to be higher than that in serum, at between 100 to 250 nM. The urine SAM concentration has been reported in the range of 20-150 μM.

In view of the importance of SAM, it is desirable to have an easy and reliable method to measure its concentration in a biological sample. Assay range and sensitivity required for measuring SAM in most common biological samples for both normal and abnormal concentrations are estimated as follows:

| | | |
|---|---|---|
| Serum/Plasma assay- | 20-300 nM | ($2.0 \times 10^{-8}$ to $3.0 \times 10^{-7}$ M) |
| Erythrocytes assay- | 600-8000 nM | ($6.0 \times 10^{-7}$ to $8.0 \times 10^{-6}$ M) |
| Whole blood assay- | 300-4000 nM | ($3.0 \times 10^{-7}$ to $4.0 \times 10^{-6}$ M) |
| CSF assay- | 30-500 nM | ($3.0 \times 10^{-8}$ to $5.0 \times 10^{-7}$ M) |
| Urine assay- | 5-300 μM | ($5.0 \times 10^{-6}$ to $3.0 \times 10^{-4}$ M) |
| Liver tissue assay- | 20-200 nmole/g tissue | |
| Cells assay- | 1-200 ng/$10^6$ cells | |

A classical assay method for measurement of SAM in rat liver utilized the tripolyphosphatase activity that was associated with S-adenosylmethionine synthetase (Y. Suma, et al, J. Biochemistry, 96, 679-682, 1984.) in rat liver. The tripolyphosphatase activity is stimulated by low concentrations of S-adenosylmethionine (Mudd, S. H., 1963, J. Biol. Chem. 238, 2156-2163.) The assay sensitivity was reported at 0.1 nmole of SAM in an assay volume of 0.1 ml (i.e., $10^{-6}$M). Samples were lyophilized, homogenized in acid, and centrifuged. The supernatant was then passed through Dowex 1 ($HCO_3^-$ form) to rid of endogenous inorganic phosphate and other potential interferents in the tissue. Great care has to be taken to avoid inorganic phosphate contamination from all reagents including the enzyme preparation, as well as glasswares.

The more common method for measuring SAM in tissues or biological fluids is HPLC or electrophoresis after sample preparation normally encompassing the protein precipitation and/or extraction (P. Giulidori and G. Stramentinoli. 1984, Anal. Biochem. 137: 217-220; Loehrer, F. M., et al. Nephrol Dial Transplant, 1998, 13: 656-661; Melnyx, S. et al. Clin Chem, 2000, 46: 265-272; E. S, Struys, et al. Clinical Chemistry, 2000, 46 (10): 1650-1656; A. Becker, et al., European J. Clin. Invest., 2003, 33: 17-25). Post column detection may include derivatization, then measurement through absorption, fluorescence, or electrochemical change, and more recently by Mass Spectrometry (MS), or Tandem Mass Spectrometry (MS/MS). Radioisotopes or stable isotopic molecules of SAM are frequently used for internal reference purpose. These methods are capable of measuring low level of SAM in serum or plasma; however, the process typically is laborious, time consuming and/or requires expensive equipments. Another drawback is that it usually does not distinguish the diastereoisomers of SAM at the sulfonium position.

SAM is produced biologically in the (S,S) configuration at the sulfonium and α-amino acid carbon, respectively. Under normal physiological conditions or storage conditions, SAM spontaneously racemizes to form a mixture of (R,S) and (S,S) isomers. Most methyltransferases are reported to be specific to the (S,S) form of SAM only.

A stereospecific colorimetric assay of SAM based on an enzyme-coupled reaction, thiopurine methyltransferase-catalyzed thiol methylation, has been developed by Sunny Zhou's group at Washington State University at Pullman, Wash. (Cannon, L. M, et al, Analytical Biochemistry, 308 (2) 358-363, 2002). The assay utilizes stereo-specific characteristics of a recombinant human thiopurine S-transmethyltransferase (TPMT, EC 2.1.1.67) and measures the change of absorbance at 410 nm of 2-nitro-5-thiobenzoic acid (TNB) vs. 2-nitro-5-methylthiobenzoic acid. The downside of the assay is that both the starting material and the product exhibits 410 nm absorption, and higher absorption associated with the starting material; therefore, the assay is effectively measuring the decrease in absorption at 410 nm. This is potentially complicated by the fact that TNB can be easily oxidized to form the disulfide, 5.5'-dithiobis-2-nitrobenzoic acid, which also has a low 410 nm absorption.

An NMR methodology was described for the determination and characterization of dietary supplement SAM without pure reference standards. A 400 MHz spectrometer is used to assess chemical structure, differentiate and determine the ratio of (S,S) and (R,S) diastereomers (G. M. Hanna, 2004, Pharmazie, 59 (4), 251-256.) The study of 10 synthetic lots showed (S,S) content ranges from 0 to 82.3%.

Recently, the necessity of differentiate diastereoisomers of SAM has been drawn to question. One study showed that both isomers gave significant activities, in terms of functional outcome, in increasing blood flow and bile production in isolated perfused rat livers (Tredger, J. M. SAMe in ischemia-reperfusion injury: experimental basis and clinical findings. 4th reunion of metabolism of methionine, Sierra Nevada, Granda, Spain, 1998; Dunne, J. B., Alexander, B., Williams, R., Tredger, J. M, and Hoffman, J. L., Evidence that SAMe diastereoisomers may reduce ischaemia-reperfusion injury by interacting with purinoceptors in isolated rate liver. Chromatographyic analysis of the chiral and covalent instability of S-adenosylmethionine. Br J Pharmacol, 1998, 125: 225-233). It is not clear whether enzymes other than methyltransferase that involved SAM are responsible for the functional activity, or a reversible racemization is contributing to this result.

Perhaps the notion that all biological methylations uses only the (S,S) diastereomer of SAM requires a more thorough examination as well. From literature we found that homocysteine S-methyltransferase has been reported as an exception capable of utilizing both diastereomers with respects to its sulfonium ion center. (J. Durell et al, 1957, Biochim. Biophys. Acta, 26, 270; V. Zappia et al, 1969, Biochim. Biophys. Acta, 178, 185.) Another recent study revealed a homocysteine methyltransferase from yeast recognized both (R,S) and (S,S) isomers; in fact one yeast preferred the (R,S) isomer as substrate, while another utilized the (R,S) isomer exclusively. The (R,S)-specific homocysteine methyltransferase activity was also shown to occur in extracts of *Arabidopsis thaliana, Drosophila melanogaster*, and *Caenorhabditis elegans* (C. R. Vinci and S. G. Clarke, Recongition of Age-damaged (R,S)-adenosyl-L-methionine by two methyltransferases in the yeast *Saccharomyces cerevisiae,* 2007, J. Biol. Chem., 282 (12), 8604-8612).

A commercial assay (for R&D purpose only), Bridge-It® S-adenosylmethionine fluorescence assay has emerged in 2007 (Mediomics, LLC, St Louis, Mo.). In the presence of SAM the activity of a unique DNA sequence-specific MetJ protein binding to DNA increases. The MetJ consensus sequence was split into two DNA "half-sites". One fragment is labeled with fluorescein and the other with Oyster® 645 fluorophore. The concentration of SAM is in direct proportion to the formation of DNA-MetJ protein complex, which resulted in two fluorophores in close proximity and allowed energy transfer to occur (Excitation at 485 nm for fluorescein and emission at 665 nm for Oyster® 645.). A dynamic range from 0.5 µM to 20 µM and detection limits of 0.5 µM were claimed.

U.S. Pat. No. 6,713,273 discloses a method for measuring SAM utilizing a recombinant S-adenosylhomocysteinase (S-adenosylhomocysteine hydrolyase, SAHH, EC 3.3.1.1) coupling with glycine N-methyltransferase (EC 2.1.1.20) and homocysteine α,γ-lyase (rHCYase). The methyltransferase converts SAM to SAH which is then hydrolyzed by SAHH to generate homocysteine. If rHCYase is also included, the homocysteine can be converted to hydrogen sulfide, α-ketoglutarate and ammonia. Either the amount of hydrogen sulfide or homocystiene generated is in direct proportion to SAM concentration in the sample. The idea of enzyme channeling is sound, but no actual example was demonstrated to show that this process indeed worked with a biological sample. An approach like this has a potentially risk of interference by the presence of endogenous compounds such as homocysteine which concentration in serum is within 5-20 µM range, an amount substantially higher than that of SAM in serum or plasma (50-150 nM).

US published patent application 2005/0003378 based on provisional application Ser. No. 60/434,397 discloses an in vitro assay for SAM as a demethylase inhibitor.

Another molecule of interest, S-Adenosylhomocysteine (SAH), is the precursor leading to the biosynthesis of SAM, as well as the product of all transmethylation reactions involving SAM as the methyl donor; i.e., SAH is metabolically linked to SAM, and structurally it contains a single carbon (as methyl) less than SAM. The co-existence and structure similarity of SAM and SAH present a great challenge to develop a method for the specific determination of the concentration of either molecule in a biological sample. The unstable (highly reactive) nature of SAM renders the level of difficulty for its determination even higher.

As the immediate precursor of all of the homocysteine (HCys) produced in the body, SAH has been raised as a possibly more sensitive indicator for the risk of vascular disease than plasma HCys recently (C. Wagner and M. Koury. Am. J. Clin Nutr 2007, 86: 1581-1585; D. Kerins, et al. Am. J. Clin Nutr 2001, 74: 723-729). The total plasma concentration of SAH is normally in the range of 15-30 nM (by contrast, plasma homocysteine is in the range of 5-15 µM). Like SAM, with no distinguished absorption, the determination of SAH in serum or plasma has been a challenge. Advanced method such as LC with post column derivatization, HPLC-MS, or HPLC-MS/MS with internal reference is a recent development for its determination. However, these methods typically involve expensive instrumentations, laborious sample preparation, and time consuming procedures. Unlike SAM, however, SAH is a relatively stable compound; the sample handling and stability are usually non-problematic.

An enzymatic method to quantify SAH in biological samples has been suggested in the art. Mutated or genetically engineered S-adenosylhomocysteine hydrolase which retains or has enhanced binding affinity toward either Hcys or SAH, and with attenuated catalytic activity has been identified or developed (U.S. Pat. No. 6,376,210; Y. Tran, et al. Clinical Chemistry, 46:1686-1688, 2000)

An antibody specific to SAH has been previously developed for the determination of serum/plasma homocysteine. In such a homocysteine assay, homocysteine was first converted to SAH via the reversible enzyme S-adenosylhomocysteine hydrolase (EC 3.3.1.1) in the presence of adenosine. Anti-SAH antibody was then used to competitively capture SAH in the assay (Homocysteine assay by Abbotts Laboratory; Homocysteine Assay by Axis-Shield ASA, Norway). Since the serum/plasma concentration of homocysteine is at 5-20 µM range, the assay sensitivity requirement for the enzymatically converted SAH is in the same ballpark. The presence of endogenous SAH (at tens nM concentration) is not an issue, neither is the cross-reactivity of the anti-SAH toward SAM because its concentration is also a couple orders of magnitude lower.

Recently an immunoassay for SAH in plasma has been reported by A. Capdevila, et al. (J Nutritional Biochemistry, 18: 827-831, 2007) utilizing Axis-Shield's anti-SAH antibody and SAH conjugate. Although the initial study of the antibody indicated some cross-reactivity toward SAM, the paper claimed SAM was not recognized even at high concentration under the current assay conditions.

Also, since SAH is the product of all methylation reactions involving SAM as methyl donor, increased concentration of SAH (or [SAH]) in tissues are frequently accompanied by decreased concentration of SAM ([SAM]). Therefore, the ratio of [SAM] and [SAH] may be a more sensitive indicator than the concentration of either SAM or SAH alone, particularly when their changes are subtle at early stages of dysfunction or abnormal conditions. The ratio of the concentration of SAM to the concentration of SAH known as "the methylation index," was first proposed by Cantani, et al. as an indicator of the methylating capacity of the cell (Inhibition of S-adenosylhomocysteine hydrolase and their role in the regulation of biological methylation. In Usdin E., Borchardt R T, Creveling C R, eds. Transmethylation. New York, N.Y. Elsevier North Holland, 1978, pages 155-164.) The ratio was later referred by M. S. Hershfield et al as "methylation index" in Cancer Res 43: 3451-3458, 1983.

Furthermore, normal SAM concentration in plasma appears to be different, greatly depending on gender (normally, men>women), individual's weight, and maybe ethnicity, and diet, etc. Similarly dependency exists for SAH concentrations since SAM and SAH are closely tied together metabolically. By utilizing the ratio of [SAM] and [SAH] it is likely these variables can be eliminated or diminished.

Connection of SAM and SAH to cardiovascular disease, depression, cancer and aging-related diseases such as Alzheimer's disease is well documented. Methylation is highly critical in fetus development, in differentiation, in epigenetic regulation of protein expression via DNA and the histone methylation. The valuation of the S-adenosylmethionine and methylation capacity index is in their scientific basis as "vitality" indicators or "wellness" markers, as opposed to homocysteine (or S-adenosylhomocysteine as some would prefer to use) as a "disease" marker.

Combining a method (e.g., an immunoassay) for quantifying SAH with the immunoassay described in the present invention will allow the determination of the so-called "methylation index", a very rapid and simple task that every medical research facility and clinical laboratory can perform.

OBJECTS OF THE INVENTION

It is a primary object of the present invention to provide novel haptens useful for the immunochemical determination of S-adenosylmethionine.

It is another object of the present invention to provide S-adenosylmethionine analogs useful for conjugation with immunogenic carriers for production of antibodies useful for immunoassays for the determination of S-adenosylmethionine.

It is a further object of the present invention to provide conjugates of S-adenosyl-methionine analogs.

It is also an object of the present invention to provide antibodies against conjugates of S-adenosylmethionine analogs.

Still, another object of the invention is to provide immunoassays useful for the qualitative and quantitative determination of S-adenosylmethionine.

It is a specific object of the present invention to provide polyclonal and monoclonal antibodies recognizing S-adenosylmethionine specifically.

A still additional object of the invention is the determination of the methylation index, [SAM]/[SAH] ratio, in a biological sample combining the immunoassay of the invention and a method (including immunoassay) to determine SAH concentration.

Other objects and embodiments of the present invention will be further discussed below.

SUMMARY OF THE INVENTION

Figure 1:
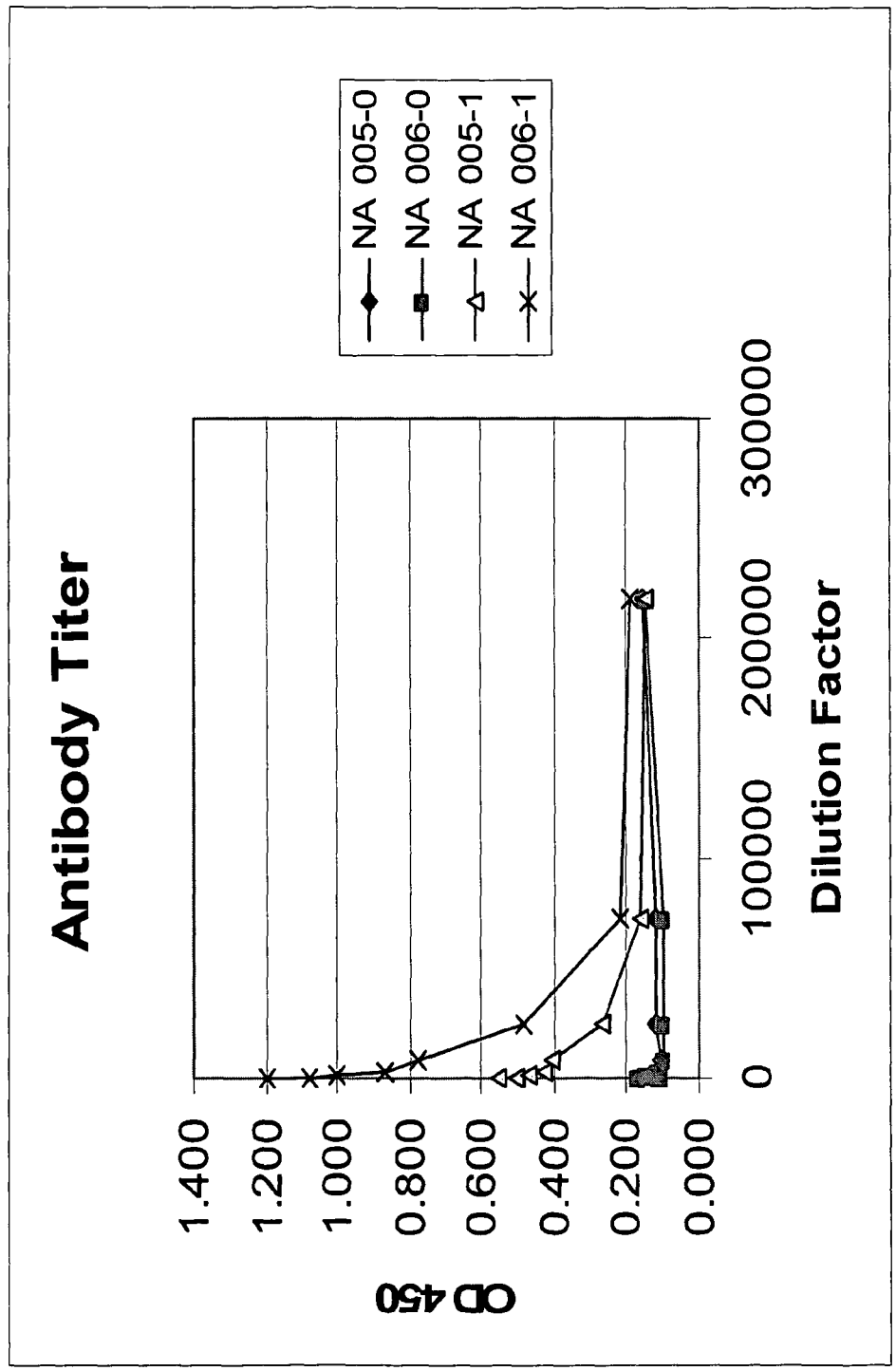
FIG. 1 shows Antibody Titer Determination. The antibody titer was determined by serial dilutions of the antiserum and evaluated on goat-anti-rabbit microwells plate/strips using hapten-HRP conjugate. The antiserum was incubated for at least 1 hr at room temperature. Upon washing, HRP conjugate was added and incubated for at least ½ hr. HRP substrate was applied after the microwells were washed and blot dry. After 15 minutes acid was added to stop the color development, and the optical density at 450 nm of each well was read with a plate reader. NA005 and 006 are animal designation numbers, 0 represents pre-bleed, 1 represents the first bleed after 4 immunizations.

In its broadest aspects, the invention provides an antibody specifically recognizing S-adenosylmethionine having a cross reactivity with S-adenosylhomocysteine and analogs thereof of less than 10%, more preferably a cross reactivity with S-adenosylhomocysteine and analogs thereof of less than 5% and most preferably having a cross reactivity with S-adenosyl-homocysteine and analogs thereof of less than 3%.

The invention also provides polyclonal and monoclonal antibodies which substantially selectively binds to SAM and analogs of SAM while not being substantially cross-reactive with SAH and analogs thereof.

The instant invention further describes antibodies useful in an immunoassay to detect or measure S-adenosylmethionine in a sample, wherein said antibodies specifically binds to S-adenosylmethionine.

The present invention provides unique antibody reagents and labeled reagents for the detection and quantification of S-adenosylmethionine or analogs thereof in a test sample. The instant invention also provides synthetic procedures for preparing haptens and immunogens which are employed for the production of such antibody reagents, and for preparing such labeled reagents. According to the present invention, the labeled reagents and the antibody reagents offer an advance in the art beyond previously known procedures for the detection and quantification of S-adenosylmethionine or analogs thereof in a test sample. According to a preferred embodiment of the present invention, labeled reagents and antibody reagents are described for use in an assay which combines the specificity of an antibody with the speed and convenience of easily automated immunoassays to provide the precise and reliable quantification of S-adenosylmethionine or analogs thereof in a test sample.

In one aspect of the invention, there is provided a method for assaying a sample for S-adenosylmethionine wherein said method comprises: (a) obtaining a sample; (b) mixing or combining said sample with antibody specific for S-adenosylmethionine; (c) detecting the binding of S-adenosylmethionine present in said sample with said antibody; and (d) quantifying the binding as a measure of the amount of S-adenosylmethionine present in said sample.

In another aspect, the invention describes an immunoassay for determining S-adenosylmethionine in a sample comprising the steps of: combining a sample suspected of containing S-adenosylmethionine with an antibody specific for S-adenosylmethionine and a labeled analyte analog, whereby the S-adenosylmethionine and the analyte analog competitively bind to the antibody, and determining the amount of labeled analog bound or unbound to the antibody as a measure of the S-adenosylmethionine in the sample.

In a further aspect, the invention provides a method of detecting or determining S-Adenosyl-methionine comprising the steps of: (a) providing a sample suspected of containing S-adenosylmethionine; (b) mixing or combining the sample with: (i) an antibody specific for S-adenosylmethionine; and (ii) optionally, an S-adenosylmethionine analogue; wherein the antibody or the S-adenosylmethionine analogue is either directly or indirectly conjugated with a label or complexed with the label by binding pair interaction and wherein said label produces a detectable signal; and (c) observing or measuring one of: (i) the signal associated with S-adenosylmethionine bound to antibody; (ii) the signal associated with S-adenosylmethionine unbound to antibody; or (iii) the total signal present; in order to detect or determine the presence or concentration of S-adenosylmethionine in the sample.

The instant invention also provides a method for determining S-adenosylmethionine in a sample comprising: (a) forming or combining a mixture comprising the sample, an antibody that binds specifically with S-adenosylmethionine to form an S-adenosylmethionine-antibody complex, and an S-adenosylmethionine analog conjugate that competes with the S-adenosylmethionine in the sample to form an S-adenosylmethionine analog-antibody complex, wherein either the antibody or the analog conjugate is attached directly or indirectly to a label that combines with either the S-adenosylmethionine or the antibody, respectively, to produce a detectable signal, and (b) determining the signal produced in step (a) as a measure of the S-adenosylmethionine in the sample.

The instant invention further provides a method for analyzing a sample of human serum or plasma to determine the presence of S-adenosylmethionine comprising the steps of: (a) providing a sample of human serum/plasma suspected of containing S-adenosylmethionine; (b) mixing with the sample (i) a tracer compound comprising an analog of S-adenosylmethionine having attached thereto a label group able to be detected, and (ii) an antibody having a high degree of specificity to S-adenosylmethionine and low cross-reactivity with S-adenosylhomocysteine; (c) determining the amount of tracer compound bound to the antibody; and (d) calculating the amount of S-adenosylmethionine present in the sample based on the amount of tracer compound bound to the antibody.

Additionally, the invention provides a process for determining the concentration of S-adenosylmethionine in a sample which comprises: (a) mixing said sample with an antibody for S-adenosylmethionine, said antibody being formed from an antigen consisting essentially of an immunogenic carrier material bonded to a compound of the formula:

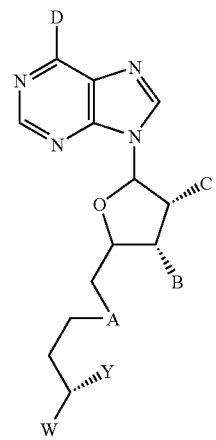

its enantiomers, diastereomers, enantiomerically enriched mixtures, racemic mixtures thereof, isotopically enriched forms thereof, crystalline forms, non-crystalline forms, amorphous forms thereof, charged and non-charged forms thereof, solvates thereof, metabolites thereof, and salts thereof, wherein A is selected from the group consisting of

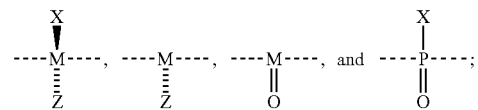

wherein M is selected from the group consisting of N, $N^+$, C, S, $S^+$, Se, $Se^+$, and P; ---- denotes the bonding location for each A group as defined above; X is independently selected from the group consisting of H, $CH_3$, $CH_2OH$, $CH_2NH_2$, OH, $OCH_3$, $NH_2$, SH, CHO, and CN; Z is independently selected from the group consisting of $CH_3$, $CH_2OH$, $CH_2NH_2$, OH, $OCH_3$, $NH_2$, SH, CHO, and CN; B and C are independently selected from the group consisting of H, OH, $NH_2$, SH, F, Cl, Br, and I; D is independently selected from the group consisting of $NH_2$, OH, SH, F, Cl, Br, and I; Y is independently selected from the group consisting of H, $CH_3$, $CH_2OH$, $CH_2NE_2$, OH, $OCH_3$, $NH_2$, SH, CHO, and CN; and W is independently selected from the group consisting of H, COOH, $CONH_2$, $COOCH_3$, CN, CHO and functionalized derivatives thereof; (b) measuring the extent of binding between said antibody and S-adenosylmethionine in said sample; and (c) comparing the measured extent of binding between said antibody and S-adenosylmethionine in said sample with a known quantitative relationship between an extent of binding and a specific concentration of S-adenosylmethionine.

The invention still further provides a method for detecting or determining S-adenosylmethionine in a sample, the method comprising contacting the sample with at least one conjugate of the hapten of formula I conjugated to a detectable labelling agent, and with at least one antibody raised against the immunogen comprising the hapten of structural formula I coupled to an antigenicity-conferring carrier material; detecting or determining bound conjugate; and deducing from the calibration curve the presence of, or the amount of, the S-adenosylmethionine in the sample.

The invention further provides a process for the detection and determination of S-adenosylmethionine which reacts with antibodies by means of a binding protein capable of reacting to bind said S-adenosylmethionine specifically, comprising the steps of: (a) providing a given quantity of the coupling product of said S-adenosylmethionine and an enzyme; (b) providing a corresponding given quantity of a specific binding protein capable of reacting to bind said S-adenosylmethionine and said S-adenosylmethionine-enzyme coupling product, and being an antibody produced by injecting the coupling product of the S-adenosylmethionine and a high molecular substance capable of stimulating antibody formation into the blood of an animal and subsequently isolating the antibody from the animal blood; (c) the nature of the coupling in the coupling product of the S-adenosylmethionine and enzyme and the coupling product of the S-adenosylmethionine and high molecular substance being chemically identical or different as a result of either (i) a chemically different bond or bridge, (ii) chemically different S-adenosylmethionines which are immunologically related, (iii) coupling via another position of the S-adenosylmethionine molecule, (iv) conjugating with or without spacer, or (v) combinations of (i), (ii), (iii) and (iv); (d) contacting a sample of a fluid containing the S-adenosylmethionine to be determined with said coupling product of the S-adenosylmethionine and enzyme and said binding protein to form a mixture; (e) separating the S-adenosylmethionine-enzyme coupling product bound to the binding protein from the unbound S-adenosylmethionine-enzyme coupling product; and (f) determining the enzyme activity of a separated portion, which activity is a measure of the quantity of S-adenosylmethionine to be determined.

The method described herein utilizes an antibody that recognizes S-adenosylmethionine (SAM) specifically. The antibody is produced against a stable analog of SAM, strategically modified on the methionine side chain, preferentially at the sulfonium position. One such antibody is illustrated in enzyme-linked immunosorbent assay (ELISA) format to demonstrate its selectivity toward SAM, and capability to determine SAM concentration from $10^{-9}$ M to $10^{-5}$ M, which is suitable for almost all biological samples as well as other non-biological applications such as determination of supplement formulation containing SAM.

The immunoassay is easy, fast, and can be automated easily. The application of the antibody can be adopted to various assay formats, and instrument platforms.

The invention also provides an immunoassay kit for the detection of S-adenosylmethionine in a sample, the immunoassay kit comprising antibodies that are specific against S-adenosylmethionine and/or analogs thereof, and immunologically acceptable reagents useful for detection or quantification of specific binding in the sample.

The invention further provides a kit for detecting or determining SAM, the kit including at least one conjugate of the hapten of structural formula I conjugated to either a detectable labelling agent, or an indirect surrogate such as avidin/biotin (detected through binding to biotin/avidin-label), or a protein (hapten-protein competes with hapten for a limited amount of antibody, then detected via complexing to a secondary antibody-label conjugate, for example); and at least one antibody raised against a hapten of structural formula I coupled to an antigenicity-conferring carrier material.

The invention is also directed to a test-kit for the detection and determination of S-adenosylmethionine comprising: (a) a given quantity of the coupling product of said S-adenosylmethionine (hapten) and an enzyme; (b) a corresponding given quantity of an immobilized specific binding protein capable of reacting to bind said S-adenosylmethionine and said S-adenosylmethionine (hapten)-enzyme coupling product, and being an antibody produced by injecting the coupling product of the S-adenosylmethionine and a high molecular substance capable of stimulating antibody formation into the blood of an animal and subsequently isolating the antibody from the animal blood; the nature of the coupling in the coupling product of the S-adenosylmethionine and enzyme and the coupling product of the S-adenosylmethionine and high molecular substance being chemically identical or different as a result of either (i) a chemically different bond or bridge, (ii) chemically different S-adenosylmethionines which are immunologically related, (iii) coupling via another position of the S-adenosylmethionine molecule, (iv) conjugating with or without spacer, or (v) combinations of (i), (ii), (iii) and (iv).

The invention is also directed to a test-kit for the detection and determination of S-adenosylmethionine comprising: (a) a given quantity of an immobilized coupling product of said S-adenosylmethionine (hapten) and a protein, a polyamino acid, or a bio-organic large molecule (antigen); (b) a corresponding given quantity of specific binding protein capable of reacting to bind said S-adenosylmethionine and said S-adenosylmethionine (hapten)-large bio-organic molecule coupling product (antigen), and being an antibody produced by injecting the coupling product of the S-adenosylmethionine and a high molecular substance capable of stimulating antibody formation into the blood of an animal and subsequently isolating the antibody from the animal blood; (c) a coupling product of a secondary binding protein and an enzyme, wherein the secondary binding protein is capable of binding to the said specific binding protein of (b).

The invention is also directed to an antibody specific to S-adenosylmethionine and analogs thereof prepared by inoculating a host animal with an immunogen comprising an immunogenic substance coupled to an S-adenosylmethionine hapten of the formula:

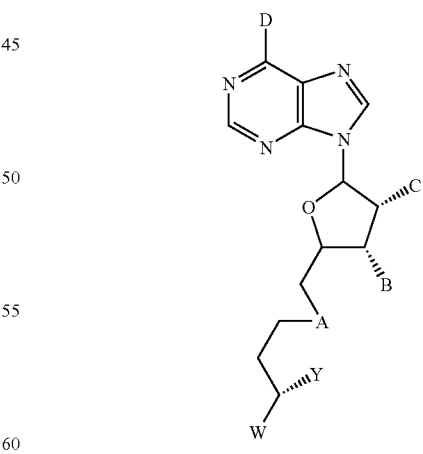

its enantiomers, diastereomers, enantiomerically enriched mixtures, racemic mixtures thereof, isotopically enriched forms thereof, crystalline forms, non-crystalline forms, amorphous forms thereof, charged and non-charged forms thereof, solvates thereof, metabolites thereof, and salts thereof; wherein A is selected from the group consisting of

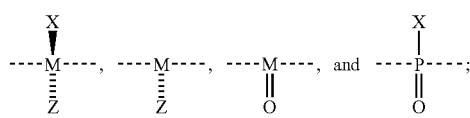

wherein M is selected from the group consisting of N, N⁺, C, S, S⁺, Se, Se⁺, and P; ---- denotes the bonding location for each A group as defined above; X is independently selected from the group consisting of H, $CH_3$, $CH_2OH$, $CH_2NH_2$, OH, $OCH_3$, $NH_2$, SH, CHO, and CN; Z is independently selected from the group consisting of $CH_3$, $CH_2OH$, $CH_2NH_2$, OH, $OCH_3$, $NH_2$, SH, CHO, and CN; B and C are independently selected from the group consisting of H, OH, $NH_2$, SH, F, Cl, Br, and I; D is independently selected from the group consisting of $NH_2$, OH, SH, F, Cl, Br, and I; Y is independently selected from the group consisting of H, $CH_3$, $CH_2OH$, $CH_2NH_2$, OH, $OCH_3$, $NH_2$, SH, CHO, and CN; and W is independently selected from the group consisting of H, COOH, $CONH_2$, $COOCH_3$, CN, CHO and functionalized derivatives thereof; and thereafter collecting serum from said host animal.

The invention further provides an immunogenic composition for raising a cross-reactive antisera to S-adenosylmethionine wherein said composition comprises an immunogen, said immunogen comprising an immunologically active carrier protein to which is bound a hapten of the formula:

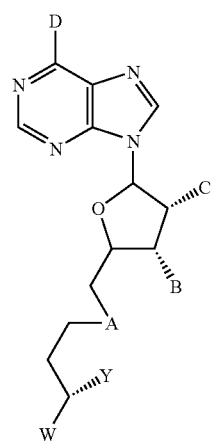

its enantiomers, diastereomers, enantiomerically enriched mixtures, racemic mixtures thereof, isotopically enriched forms thereof, crystalline forms, non-crystalline forms, amorphous forms thereof, charged and non-charged forms thereof, solvates thereof, metabolites thereof, and salts thereof; wherein A is selected from the group consisting of

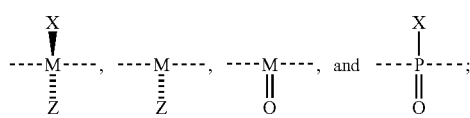

wherein M is selected from the group consisting of N, N⁺, C, S, S⁺, Se, Se⁺, and P; ---- denotes the bonding location for each A group as defined above; X is independently selected from the group consisting of H, $CH_3$, $CH_2OH$, $CH_2NH_2$, OH, $OCH_3$, $NH_2$, SH, CHO, and CN; Z is independently selected from the group consisting of $CH_3$, $CH_2OH$, $CH_2NH_2$, OH, $OCH_3$, $NH_2$, SH, CHO, and CN; B and C are independently selected from the group consisting of H, OH, $NH_2$, SH, F, Cl, Br, and I; D is independently selected from the group consisting of $NH_2$, OH, SH, F, Cl, Br, and I; Y is independently selected from the group consisting of H, $CH_3$, $CH_2OH$, $CH_2NH_2$, OH, $OCH_3$, $NH_2$, SH, CHO, and CN; and W is independently selected from the group consisting of H, COOH, $CONH_2$, $COOCH_3$, CN, CHO and functionalized derivatives thereof.

The present invention also provides a compound of the formula I

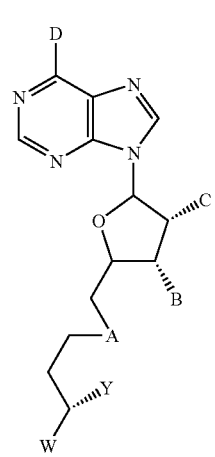

its enantiomers, diastereomers, enantiomerically enriched mixtures, racemic mixtures thereof, isotopically enriched forms thereof, crystalline forms, non-crystalline forms, amorphous forms thereof, charged and non-charged forms thereof, solvates thereof, metabolites thereof, and salts thereof; wherein A is selected from the group consisting of

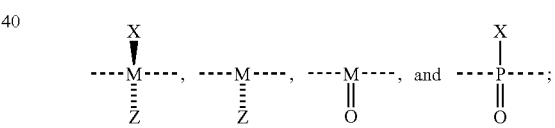

where M is selected from the group consisting of N, N⁺, C, S, S⁺, Se, Se+ and P, ---- denotes the bonding location for each A group as defined above; X is independently selected from the group consisting of H, $CH_3$, $CH_2OH$, $CH_2NH_2$, OH, $OCH_3$, $NH_2$, SH, CHO, and CN; Z is independently selected from the group consisting of $CH_3$, $CH_2OH$, $CH_2NH_2$, OH, $OCH_3$, $NH_2$, SH, CHO, and CN; B and C are independently selected from the group consisting of H, OH, $NH_2$, SH, F, Cl, Br, and I; D is independently selected from the group consisting of $NH_2$, OH, SH, F, Cl, Br, and I; Y is independently selected from the group consisting of H, $CH_3$, $CH_2OH$, $CH_2NH_2$, OH, $OCH_3$, $NH_2$, SH, CHO, and CN; and W is independently selected from the group consisting of H, COOH, $CONH_2$, $COOCH_3$, CN, CHO and functionalized derivatives thereof.

The invention also provides a hapten of formula I as shown above and a method for preparing said hapten.

The invention further provides an immunogen comprising a hapten of structural formula I, coupled directly or indirectly to an antigenicity-conferring carrier material. The invention further provides an antibody raised against the immunogen wherein the antibody is capable of binding and recognizing S-adenosylmethionine specifically. The invention also provides a hapten conjugated directly or indirectly to a detectable labelling agent.

The instant invention also provides a hapten useful for generating antibodies against S-adenosylmethionine said hapten having an analogous chemical structure to S-adenosylmethionine and having a positive charge at the methionine or methionine equivalent and chemically analogous moieties.

The invention also includes novel compounds of the formula I

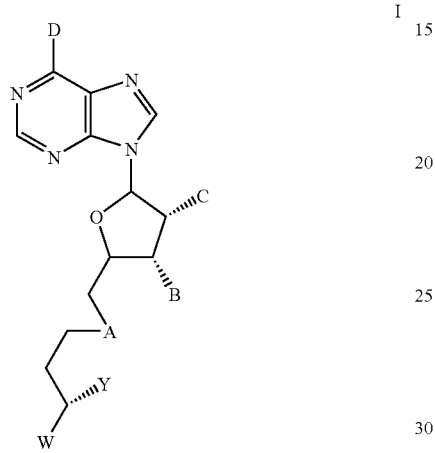

its enantiomers, diastereomers, enantiomerically enriched mixtures, racemic mixtures thereof, crystalline forms, non-crystalline forms, amorphous forms thereof, charged and non-charged forms thereof, solvates thereof, metabolites thereof, and salts thereof, wherein A is selected from the group consisting of

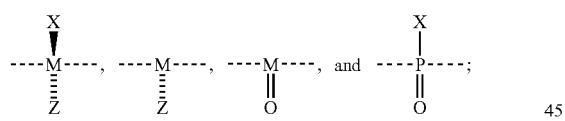

where M is selected from the group consisting of N, $N^+$, C, S, $S^+$, Se, $Se^+$ and P, ---- denotes the bonding location for each A group as defined above; X is independently selected from the group consisting of H, $CH_3$, $CH_2OH$, $CH_2NH_2$, OH, $OCH_3$, $NH_2$, SH, CHO, and CN;

Z is independently selected from the group consisting of $CH_3$, $CH_2OH$, $CH_2NH_2$, OH, $OCH_3$, $NH_2$, SH, CHO, and CN;

B and C are independently selected from the group consisting of H, OH, $NH_2$, SH, F, Cl, Br, and I;

D is independently selected from the group consisting of $NH_2$, OH, SH, F, Cl, Br, and I;

Y is independently selected from the group consisting of H, $CH_3$, $CH_2OH$, $CH_2NH_2$, OH, $OCH_3$, $NH_2$, SH, CHO, and CN; and W is independently selected from the group consisting of H, COOH, $CONH_2$, $COOCH_3$, CN, CHO and functionalized derivatives thereof with the proviso that said compound of formula I can not be

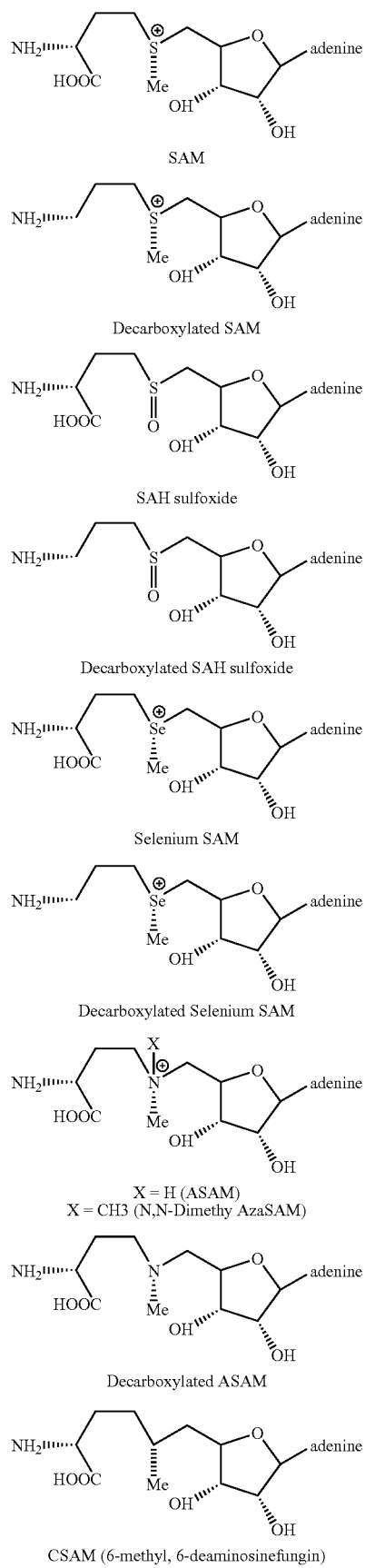

-continued

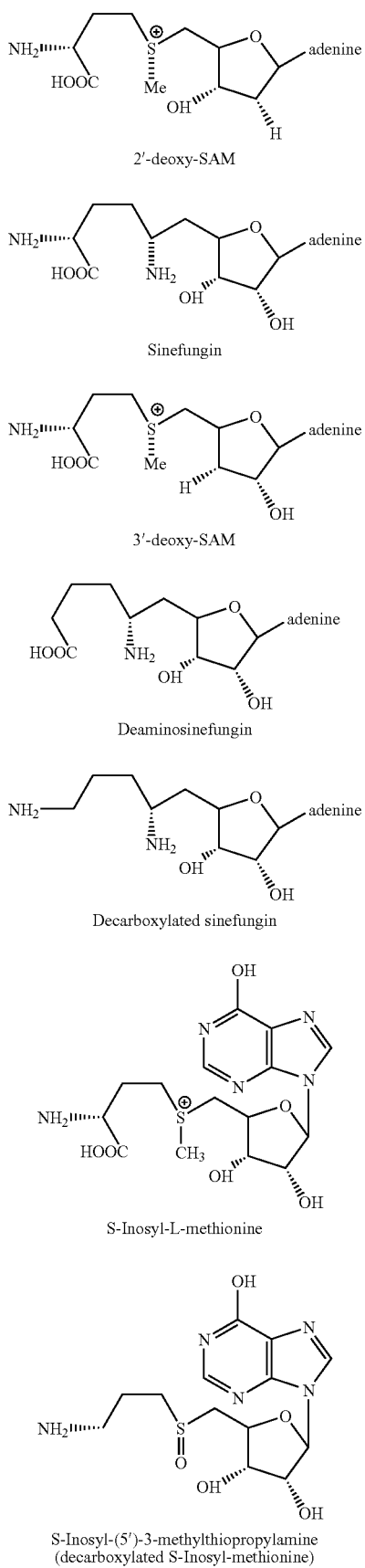

2'-deoxy-SAM

Sinefungin

3'-deoxy-SAM

Deaminosinefungin

Decarboxylated sinefungin

S-Inosyl-L-methionine

S-Inosyl-(5')-3-methylthiopropylamine
(decarboxylated S-Inosyl-methionine)

-continued

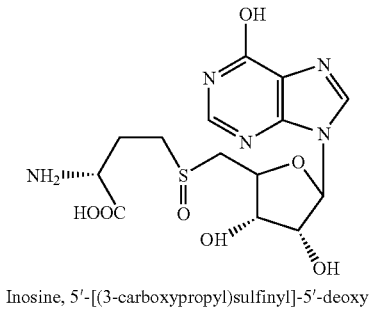

Inosine, 5'-[(3-carboxypropyl)sulfinyl]-5'-deoxy

Definitions

Throughout the present specification the following definitions are to be understood:

"Haptens" are partial or incomplete antigens. They are protein-free substances, mostly low molecular weight organic compounds, which are not capable of stimulating antibody formation, but which do react with antibodies. The latter are formed by coupling the hapten to a high molecular weight immunogenic carrier using conventional conjugate chemistry (as further explained below) and then injecting this coupled product, i.e., immunogen, into a human or animal subject. The hapten of this invention is a compound corresponding to formula I.

The terms "immunogen" and "immunogenic" refer to substances capable of eliciting, producing, or generating an immune response in a living mammal.

The term "conjugate" refers to any substance formed from the joining together of two parts. Representative conjugates in accordance with the present invention include those formed by the joining together of a small molecule, such as the compound of formula I and a large molecule, such as a carrier or a polyamino acid or polyamine polymer, particularly a protein. In the conjugate the small molecule maybe joined at one or more active sites on the large molecule directly or indirectly through a spacer through or linking agent. The term conjugate includes the term immunogen.

As used herein, a "spacing group" or "spacer" refers to a portion of a chemical structure which connects two or more substructures such as haptens, carriers, immunogens, labels, or tracers through a $CH_2$ or a functional linking group. These spacer groups will be enumerated hereinafter in this application. The atoms of a spacing group and the atoms of a chain within the spacing group are themselves connected by chemical bonds.

The term "linker" refers to a chemical moiety that connects a hapten to a carrier, immunogen, label, tracer or another linker. Linkers may also be used to attach antibodies to labels or solid substrates. Linkers may be straight or branched, saturated or unsaturated carbon chains. They may also include one or more heteroatoms within the chain or at the termini of the chains. By heteroatoms is meant atoms other than carbon which are chosen from the group consisting of oxygen, nitrogen, sulfur, phosphorus, boron and halogen. The use of a linker may or may not be advantageous or needed, depending on the specific hapten and carrier pairs. Methods and techniques for the attachment of a linker to an antibody are known in the art. For a good treatise on this subject, the reader is referred to Bioconjugate Techniques, G. Hermanson, Academic Press, 1996.

Among the preferred spacers are straight or branched, saturated or unsaturated, carbon chains. Theses carbon chains may also include one or more heteroatoms within the chain or at termini of the chains. By "heteroatoms" is meant atoms other than carbon which are chosen from the group consisting of oxygen, nitrogen, sulfur, phosphorus, boron and halogen. Spacing groups may also include cyclic or aromatic groups as part of the chain or as a substitution on one of the atoms in the chain.

The number of atoms in the spacing group is determined by counting the atoms other than hydrogen. The number of atoms in a chain within a spacing group is determined by counting the number of atoms other than hydrogen along the shortest route between the substructures being connected. A functional linking group may be used to activate, e.g., provide an available functional site on, a hapten or spacing group for synthesizing a conjugate of a hapten with a label or carrier or polyamine polymer. Common functionalities in forming a covalent bond between the linking group and the molecule to be conjugated are alkylamine, amidine, thioamide, ether, urea, thiourea, guanidine, azo, thioether and carboxylate, sulfonate, and phosphate esters, amides and thioesters. Various linking agents are well known in the art; see, for example, Cautrecasas, J. Biol. Chem. (1970) 245:3059, and Cross-Linking Reagents, Technical Handbook by Pierce Company (Rockford, Ill.)

An "immunogenic carrier," as the terms are used herein, is an immunogenic substance, commonly a protein, that can join with a hapten, in this case or the derivatives hereinbefore described, thereby enabling these hapten derivatives to induce an immune response and elicit the production of antibodies that can bind specifically with these haptens. The immunogenic carriers and the linking groups will be enumerated hereinafter in this application. Among the immunogenic carrier substances are included proteins, glycoproteins, complex polyamino-polysaccharides, particles, and nucleic acids that are recognized as foreign and thereby elicit an immunologic response from the host. The polyamino-polysaccharides may be prepared from polysaccharides using any of the conventional means known for this preparation. Also various protein types may be employed as a poly(amino acid) immunogenic carrier. These types include albumins, serum proteins, lipoproteins, etc. Illustrative proteins include bovine serum albumin (BSA), bovine γ-globulin (BgG), keyhole limpet hemocyanin (KLH), egg ovalbumin, bovine thyroglobulin (BTG), etc. Alternatively, synthetic poly(amino acids), polymerized protein or cross-linked protein may be utilized.

Immunogenic carriers can also include poly aminopolysaccharides, which are a high molecular weight polymer built up by repeated condensations of monosaccharides. Examples of polysaccharides are starches, glycogen, cellulose, carbohydrate gums such as gum arabic, agar, and so forth. The polysaccharide also contains polyamino acid residues and/or lipid residues.

The immunogenic carrier can also be a poly(nucleic acid) either alone or conjugated to one of the above mentioned poly(amino acids) or polysaccharides.

The immunogenic carrier can also include solid particles. The particles are generally at least about 0.02 microns (μm) and not more than about 100 μm, and usually about 0.05 μm to 10 μm in diameter. The particle can be organic or inorganic, swellable or non-swellable, porous or non-porous, optimally of a density approximating water, generally from about 0.7 to 1.5 g/mL, and composed of material that can be transparent, partially transparent, or opaque. The particles can be biological materials such as cells and microorganisms, including non-limiting examples such as erythrocytes, leukocytes, lymphocytes, hybridomas, *Streptococcus, Staphylococcus aureus, E. coli*, and viruses. The particles can also be comprised of organic and inorganic polymers, liposomes, latex, phospholipid vesicles, or lipoproteins.

"Poly(amino acid)" or "polypeptide" is a polyamide formed from amino acids. Poly(amino acids) will generally range from about 2,000 molecular weight, having no upper molecular weight limit, normally being less than 10,000,000 and usually not more than about 600,000 daltons. There will usually be different ranges, depending on whether an immunogenic carrier or an enzyme is involved.

A "peptide" is any compound formed by the linkage of two or more amino acids by amide (peptide) bonds, usually a polymer of α-amino acids in which the .alpha.-amino group of each amino acid residue (except the $NH_2$ terminus) is linked to the .alpha.-carboxyl group of the next residue in a linear chain. The terms peptide, polypeptide and poly(amino acid) are used synonymously herein to refer to this class of compounds without restriction as to size. The largest members of this class are referred to as proteins.

A "label," "detector molecule," or "tracer" is any molecule which produces, or can be induced to produce, a detectable signal. The label can be conjugated to an analyte, immunogen, antibody, or to another molecule such as a receptor or a molecule that can bind to a receptor such as a ligand, particularly a hapten. Non-limiting examples of labels include radioactive isotopes, enzymes, enzyme fragments, enzyme substrates, enzyme inhibitors, coenzymes, catalysts, fluorophores, dyes, chemiluminescers, luminescers, or sensitizers; a non-magnetic or magnetic particle, a solid support, a liposome, a ligand, or a receptor.

The term "antibody" refers to a specific protein binding partner for an antigen and is any substance, or group of substances, which has a specific binding affinity for an antigen to the exclusion of other substances. The generic term antibody subsumes polyclonal antibodies, monoclonal antibodies and antibody fragments such as fab, fab' and $(fab')_2$, etc., and application products containing these materials such as chimeric antibody, or humanized antibody, etc.

The term "monoclonal antibody" is meant to refer to immunoglobulins which arise from a single clone of B-lymphocyte cells and which are initially obtained by fusing a single B-lymphocyte with a myeloma tumor cell.

In the present specification, antibody specificity refers to the property of an antibody which enables it to recognize or react or bind to some particular antigenic determinants and not others. Specificity is dependent on chemical composition, physical forces, and molecular structure at the binding site.

The term "derivative" refers to a chemical compound or molecule made from a parent compound by one or more chemical reactions.

The term "carrier" refers to solid particles and/or polymeric polymers such as immunogenic polymers such as those mentioned above. Where the carrier is a solid particle, the solid particle may be bound, coated with or otherwise attached to a polyamine polymer to provide one or more reactive sites for bonding to a terminal functional group in the compounds of formula I.

The term "reagent kit," or "test kit," refers to an assembly of materials that are used in performing an assay. The reagents can be provided in packaged combination in the same or in separate containers, depending on their cross-reactivities and stabilities, and in liquid or in lyophilized form. The amounts and proportions of reagents provided in the kit can be selected so as to provide optimum results for a particular application. A reagent kit embodying features of the present invention comprises antibodies specific for compounds of formula I comprise ligands of the analyte and calibration and control materials. The reagents may remain in liquid form or may be lyophilized.

The phrase "calibration and control materials" refers to any standard or reference material containing a known amount of a compound to be measured. The concentration of compound is calculated by comparing the results obtained for the unknown specimen with the results obtained for the standard. This is commonly done by constructing a calibration curve.

"Test sample", as used herein, refers to a sample to be tested for the presence of S-adenosylmethionine and/or analogs thereof. The test sample is typically in liquid form.

The term "biological sample" includes, but is not limited to, any quantity of a substance from a living organism or formerly living organism. Such living organisms include, but are not limited to, humans, mice, monkeys, rats, rabbits, horses, and other animals, and plants, bacteria, or fungi, etc. Such substances include, but are not limited to, blood, serum, plasma, urine, cells, organs, tissues, bone, bone marrow, lymph, lymph nodes, synovial tissue, chondrocytes, synovial macrophages, endothelial cells, and skin.

DESCRIPTION OF THE PREFERRED EMBODIMENTS

In a first embodiment, the invention provides a process for determining the concentration of S-adenosylmethionine in a sample of biological fluid which comprises: (a) mixing said sample with an antibody for S-adenosylmethionine, said antibody being formed from an antigen consisting essentially of an immunogenic carrier material bonded to a compound of the formula:

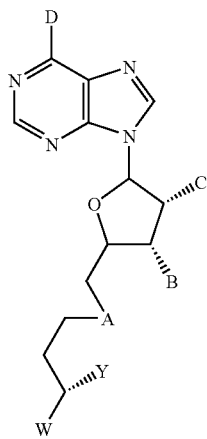

its enantiomers, diastereomers, enantiomerically enriched mixtures, racemic mixtures thereof, isotopically enriched forms thereof, crystalline forms, non-crystalline forms, amorphous forms thereof, charged and non-charged forms thereof, solvates thereof, metabolites thereof, and salts thereof; wherein A is selected from the group consisting of

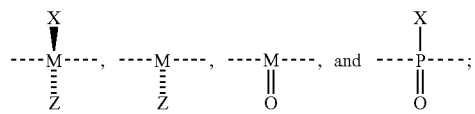

wherein M is selected from the group consisting of N, N$^+$, C, S, S$^+$, Se, Se$^+$, and P; ---- denotes the bonding location for each A group as defined above; X is independently selected from the group consisting of H, $CH_3$, $CH_2OH$, $CH_2NH_2$, OH, $OCH_3$, $NH_2$, SH, CHO, and CN; Z is independently selected from the group consisting of $CH_3$, $CH_2OH$, $CH_2NH_2$, OH, $OCH_3$, $NH_2$, SH, CHO, and CN; B and C are independently selected from the group consisting of H, OH, $NH_2$, SH, F, Cl, Br, and I; D is independently selected from the group consisting of $NH_2$, OH, SH, F, Cl, Br, and I; Y is independently selected from the group consisting of H, $CH_3$, $CH_2OH$, $CH_2NH_2$, OH, $OCH_3$, $NH_2$, SH, CHO, and CN; and W is independently selected from the group consisting of H, COOH, $CONH_2$, $COOCH_3$, CN, CHO and functionalized derivatives thereof; (b) measuring the extent of binding between said antibody and S-adenosylmethionine in said sample; and (c) comparing the measured extent of binding between said antibody and S-adenosylmethionine in said sample with a known quantitative relationship between an extent of binding and a specific concentration of S-adenosylmethionine.

Furthermore, the present invention also relates to an assay to determine the concentration of SAM in solutions, particular those derived from biological sources. The assay involves antibody specifically produced against an SAM analog modified on the methionine side chain; preferentially modified at the sulfonium center. Such an assay demonstrated that it is possible to quantify SAM in the range where most samples of biological origin lies, and in the presence of the structurally analogous S-adenosylhomocysteine (SAH) which is the precursor of SAM biosynthesis as well as the product of the transmethylation process. The method is simple and easy to perform, and provides an important tool to study the rise and fall of the SAM concentration, its equilibrium status in human body, and its association with life development and degeneration process.

Generally the invention is directed toward immunoassay utilizing an antibody produced against an immunogen containing an analog of SAM (hapten), which is particularly modified at the methionine side chain, more specifically modified at the sulfonium center. Example of the SAM analog hapten includes substituting the sulfur with nitrogen, or carbon, or selenium, or phosphorus; preferably, nitrogen (aza-adenosyl methionine). The amino acid side chain can be intact as that in SAM or simplified to aminopropyl (decarboxylated), or simply butyric acid (deamino); preferably, butyric acid for ease of derivatization and preparation as well as conjugation.

Other haptens can be derived by modifying one or both of the hydroxyl's on the ribose to amino or sulfhydryl, or deoxy, or halogen or utilizing well-known chemistry such as oxidative cleavage of 2',3'-hydroxyl with periodate, coupling the resulting dialdehyde with amino groups of the protein and completed with reductive amination. Modification can also be easily achieved by changing the 6-amino group of the adenine moiety to hydroxyl, or sulfhydryl, or by carrying out azo-coupling at the C8 position, for example.

The preferred haptens of the invention are selected from the group consisting of the following chemical structures:

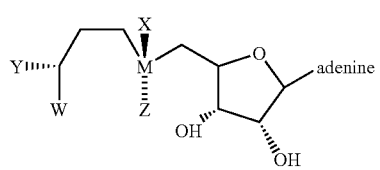

II

X = Y = H, CH$_3$, CH$_2$OH, CH$_2$NH$_2$, OH, OCH$_3$, NH$_2$, SH
Z = CH$_3$, CH$_2$OH, CH$_2$NH$_2$, OH, OCH$_3$, NH$_2$, SH
W = H, COOH, CONH$_2$, COOCH$_3$, CN, derivatives M = N, $\overset{+}{N}$, C

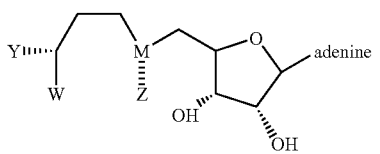

III

Y = H, CH$_3$, CH$_2$OH, CH$_2$NH$_2$, OH, OCH$_3$, NH$_2$, SH
Z = CH$_3$, CH$_2$OH, CH$_2$NH$_2$, OH, OCH$_3$, NH$_2$, SH
W = H, COOH, CONH$_2$, COOCH$_3$, CN, derivatives M = $\overset{\oplus}{S}$, $\overset{\oplus}{Se}$, P

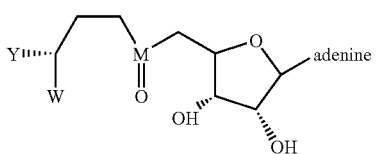

IV

Y = H, CH$_3$, CH$_2$OH, CH$_2$NH$_2$, OH, OCH$_3$, NH$_2$, SH
W = H, COOH, CONH$_2$, COOCH$_3$, CN, derivatives

M = C, S

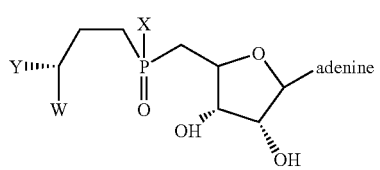

V

X = Y = H, CH$_3$, CH$_2$OH, CH$_2$NH$_2$, OH, OCH$_3$, NH$_2$, SH
W = H, COOH, CONH$_2$, COOCH$_3$, CN, derivatives More preferably, the hapten has the structure that either contains or readily presents a positive charge (through equilibrium or in the binding site micro-environment) at the position A of the formula I. The positive charge may either be at the position of M as in the case of SAM, Selenium SAM and aza-SAM (ASAM, nitrogen replacing sulfur), or at the positions of X or Z, as in the case of sinefungin (C—NH$_3^+$ replacing S$^+$—CH$_3$).

Even more preferably, the hapten is a stable compound and either contains or readily presents a positive charge at the position M. Examples of such haptens are ASAM, decarboxylated ASAM, and deamino-ASAM (AdaM), etc. Among them many are novel compounds; AdaM is one such compound.

A hapten can directly or indirectly (via a spacer or linker) be coupled to a carrier protein to form immunogen or hapten-enzyme conjugate. Hapten can also be linked to other non-enzymatic reporter group such as a chromogen, a fluorescent compound, a phosphorescent compound or a chemiluminescent material, etc. The linkage may be through carboxylic acid or phosphoric acid and alcohol to form an ester, carboxyl and amino group to form amide bond, sulfhydryl (mercaptan) and activated olefin, halogen, or other alkylating agents to form thioether, or any other bio-conjugation chemistry as illustrated in the literature of conjugation chemistry. Additionally, the carrier can be coupled to the compounds of the invention via the functional groups in the ribose or the adenine moiety.

The haptens of the invention are employed in the preparation of immunogens by coupling them to modified or non-modified antigenicity-conferring carrier materials to provide immunogens for antibody production and conjugates (tracers) that have excellent sensitivity and specificity for the detection or determination of SAM. The carrier material typically is a protein, a protein fragment, a synthetic polypeptide or a semi-synthetic polypeptide.

Illustrative examples of useful carrier materials are bovine serum albumin (BSA), egg ovalbumin, bovine gamma globulin, thyroxine binding globulin, keyhole limpet haemocyanin (KLH) etc. Alternatively, synthetic poly(amino acids) having a sufficient number of available amino groups, such as lysine, may be employed, as may other synthetic or natural polymeric materials bearing reactive functional groups. In particular, carbohydrates, yeasts or polysaccharides may be conjugated to the hapten to produce an immunogen.

Any common reporter enzyme (e.g., alkaline phosphatase or AP, and β-galactosidase or β-gal, horseradish peroxidase or HRP, etc.) can be use for preparation of hapten-enzyme conjugate. For specific application, hapten may be coupled to antibody, or biotin/avidin (or streptavidin), etc. Antibody can be a monoclonal antibody or a polyclonal antibody.

The immunogens obtained are then administered to mammalian hosts to elicit production of specific antibodies, i.e, polyclonal antibodies or monoclonal antibodies, which are then used to develop immunoassays for the determination of SAM.

The immunogen is administered to animals such as rabbits, mice, rats, chickens, sheep, goats, or cows, etc. by a series of injections according to techniques generally known in the art. An antibody, according to the present invention, is raised in response to an immunogen of the invention which is derived from a substantially purified hapten including optically pure hapten of the invention. Both polyclonal and monoclonal antibodies recognize specific epitopes on an immunogen, and, while typically polyclonal antibodies have been utilized in the present invention, both may be suitable. Polyclonal antibodies consist of a mixture of multiple antibodies, each recognizing a specific epitope, whereas monoclonal antibodies are produced by cells secreting a single antibody recognizing a specific epitope. Techniques for preparing polyclonal antibodies generally are well known in the art.

Monoclonal antibodies may be prepared by injecting animals, such as mice or rats, intraperitoneally, subcutaneously, intravenously, or in some other manner, with an antigen, namely an immunogen corresponding to compounds having formula (I) above linked to an immunogenic carrier, to elicit an immune response in the animals (namely, the production of antibodies which are specific for the antigen). Sera from the animals are drawn, and the sera are tested to determine the titer of antibody in the sera (to determine whether or not the animal elicited the desired immune response, and to what extent). Those animals in which the desired immune response has been produced are permitted to rest for approximately three weeks to three months for clearance of circulating antibodies. After this three weeks to three-month period of time, and approximately three days prior to the anticipated fusion of B-lymphocyte cells (cells which, upon stimulation by antigen, mature into plasma cells which synthesize antibody, and which are also referred to as B cells) with myeloma cells (tumor cells), a boost injection (intravenously preferred) of the antigen is administered to these animals. B-lymphocyte cells are then removed from the spleens and/or lymph nodes of these animals by standard procedures, and the B-lymphocyte cells are then fused with myeloma fusion partners according to standard procedures, such as those described in Ed Harlow and David Lane, "Antibodies, A Laboratory Manual," Cold Spring Harbor Laboratory, 1988, and in Kohler and Milstein, "Continuous Culture of Fused Cells Secreting Antibody of Predefined Specificity," Nature, 256, 495 (1975). The B-lymphocyte-myeloma fusions are then plated in multiwell tissue culture plates containing HAT media, or other suitable media. The resulting cultures are fed with HT media, or other suitable media, and fetal bovine serum or calf serum on or about the fifth and seventh days after the fusion of the cells and then tested on or about the tenth day after the fusion for the presence of antibody which is specific for the antigen. Specific desirable hybrids are then cloned by limiting dilution (Hybrid cells are diluted in differing amounts of HT media, or other suitable media, and plated out in tissue culture plates in order to isolate a single desired clone.) Established clones are then retested for specificity to a broader panel of cross reactants.

The amount of the resulting monoclonal antibodies produced by a desired clone can then be scaled up to produce a sufficient quantity of antibody for purification in either: (1) tissue culture (by expanding the number of cells in tissue culture, or HT media); or (2) mice for ascites. The monoclonal antibodies can be scaled up in mice by injecting hybrid cells into the abdominal cavity of mice and allowing the cells to grow (usually for about 7 days). The ascites is harvested from the mice by sacrificing the mice, collecting the ascites fluid, and purifying the ascites fluid. BALB/c mice are the most common strain of laboratory mouse used for this process, and they can be obtained from any mouse vendor. Pristane, should be injected into the mice to stimulate their immune systems to produce B and T cells (about two or three weeks before the hybrid cells are injected into the mice) which serve as a feeder layer for the clone cells that are injected into the mice. This is performed to provide a suitable environment in which the hybrid cells can grow.

The antibody fragments comprise a portion of an intact antibody, generally the antigen binding or variable region of the intact antibody. Examples of antibody fragments include Fab, Fab', F(ab')$_2$, and Fc fragments; diabodies; linear antibodies; single-chain antibody molecules; and multispecific antibodies formed from antibody fragments.

The antibody application derivatives and products are intended to include chimeric antibodies, humanized antibodies, genetically engineered or modified antibody sequences by site specific mutagenesis.

The invention also provides an immunoassay for determining the presence or amount of SAM in biological samples—an improvement on simplicity and efficiency over other known methods for the determination of SAM in biological samples and non-biological samples. An improved immunoassay of the invention includes a step of contacting the sample to be determined with antibodies raised in response to an immunogen of the invention. It is contemplated that any immunoassays for SAM utilizing haptens, immunogens, and/or antibodies raised against immunogens, according to the invention, are within the scope of the present invention. Examples of immunoassays include radioimmunoassays (RIAs), enzyme immunoassay (EIAs), enzyme-linked-immunosorbent assays (ELISAs) and fluorescent polarization immunoassays (FPIAs), etc. Comprehensive reviews on immunoassay principles, critical components, and assay designs can be readily found in literature. One example is "The Immunoassay Handbook, 3$^{rd}$ Edition" by David Wild, Editor (Elsevier Science, 2005), another is "Immunoassay," E. P. Diamandis and T. K. Christopoulos, Editors, Academic Press, Inc., 1996.

The immunoassays of the invention may be heterogeneous and homogeneous. In heterogeneous assays, the purpose of the label is simply to establish the location of the molecule to which it is conjugated—i.e. to establish whether the labeled molecule is free in solution or is part of a bound complex. Heterogeneous assays generally function by explicitly separating bound antigen-antibody complexes from the remaining free antigen and/or antibody. A method which is frequently employed consists of attaching one of the members of the homologous pair to a solid surface by covalent binding, physical absorption, or some other means. When antigen-antibody binding occurs, the resulting bound complexes remain attached to this solid surface (composed of any suitably inert material such as plastic, paper, glass, metal, polymer gel, etc.), allowing for separation of free antigen and/or antibody in the surrounding solution by a wash step. A variation on this method consists of using small (typically 0.05 to 20 microns) suspendable particles to provide the solid surface onto which either antigen or antibody is immobilized. Separation is effected by centrifugation of the mixture of sample, reagents and suspendable beads at an appropriate speed, resulting in selective sedimentation of the support particles together with the bound complexes. Alternative solid capture phases such as magnetic particles, glass beads, plastic tubes, glass tubes, glass wool, and latex beads, etc., have also been used.

The capture mechanism can be simply by binding to immobilized secondary antibody or an antigen, or utilize avidin/streptavidin-biotin type of binding pairs. Complimentary DNA/RNA or oligos, and other natural or man-made binding pairs can be adapted to capture the signals from the rest of the assay mixture.

Signal reporting can be UV or visible light, fluorescence, luminescence, photon, gold sol, and chemiluminescence, etc. Furthermore, application of such an antibody include assay variation which utilizes latex beads, liposome, vesicles, and alike to carry signals or signal precursors, and utilize channeling processes, or PCR and alike methods to amplify signals. Furthermore, assay format that are semi-heterogeneous or qusai-heterogeneous (e.g. Roche's Elecsys assay), can also be applied to the assays of the invention.

Use of an enzyme as a label has produced a variety of useful enzyme immunoassays (EIA), the most popular of which is known as ELISA. For a review, see "Enzyme Immunoassay (EIA)/Enzyme-Linked Immunosorbant Assay (ELISA)" by Rudolf M. Lequin, apppered in Clinical Chemistry, 51: 2415-2418, 2005. In one typical heterogeneous format where a competition reaction is employed, in which the ligand of interest, SAM as in the current invention, binds to the specific antibody-enzyme conjugate. After suitable incubation, any remaining free enzyme conjugate is eliminated by washing or other separation methods. A suitable substrate for the enzyme is then brought into contact with the surface containing the bound complexes. The enzyme-substrate pair is chosen to provide a reaction product which yields a readily detectable signal, such as a color change or a fluorescence emission. The use of an enzyme as a label services to effectively amplify the contribution of a single labeled bound complex to the measured signal, because many substrate molecules can be converted by a single enzyme molecule.

In another type of assay, an enzyme is covalently coupled to avidin/streptavidin and the resulting enzyme labeled avidin/strepavidin is then mixed or combined with biotin-labeled reagent (i.e., biotin-labeled ligand or biotin-labeled specific binding substance for said ligand) prior to or during utilization of the latter in a specific binding reaction. The basic components in the binding reaction are, in addition to the biotin-labeled reagent, liquid medium or sample (presumed to contain the ligand to be detected) and an insoluble phase containing a specific binding substance for said ligand. The biotin-labeled reagent may be bound to enzyme labeled avidin/streptavidin after it has been mixed or combined with the insoluble phase or, alternatively, the biotin labeled reagent may be pre-combined with enzyme labeled avidin and the resulting conjugate used directly.

Following the specific binding reaction, the enzyme activity of either the insoluble phase or the liquid phase is determined by a suitable detection system; the amount of activity being related to the quantity of ligand in the sample.

For immunoassays with no separation of bound vs. unbound species (homogeneous assays), Enzyme-Mediated Immunoassay (EMIT) exemplifies such an approach. Based on the functional change of an enzyme such as glucose-6-phoshate dehydrogenase, or G6PDH (commonly shown in diminishing activity) of the hapten-enzyme conjugate when bound to the specific antibody, the assay is achieved by contacting sample with an appropriate amounts of antibody and hapten-enzyme conjugate. When there is a large quantity of analyte in the sample, few of the hapten-enzyme conjugates are bound to the antibody (i.e., minimal amount of enzyme activity is attenuated) and the assay mixture exhibits maximal enzyme activity turning over maximal amount of substrate NAD (or NADP) to NADH (or NADPH). By contrast, when there is little analyte present, majority of the hapten-enzyme conjugates are bound to antibody, and the assay mixture thus reports substantially reduced signal due to diminished enzyme activity.

A couple of ELISA assays were used to demonstrate the application of SAM-specific antibody in the present invention to show assay range, sensitivity, and specificity. The assay format is provided for illustration, not for limitation. The ELISA assays used to demonstrate the invention utilize the following two formats having the reagents specified below:

ELISA Assay Format 1:

(1) Sample or calibrator(s)

(2) Antibody (3) Hapten-Enzyme Conjugate (4) Secondary antibody coated strips/microtiter plates (Examples of secondary antibody: goat-anti-mouse antibody or goat-anti-rabbit antibody)

(5) Wash solution (6) Substrate(s).

(7) Stopping reagent (optional if "end point" mode is used; for "rate" mode there is no need of a stopping reagent.)

ELISA Assay Format 2:

(1) Sample or calibrator(s)

(2) Antibody (3) Secondary antibody-Enzyme Conjugate (4) Immunogen (Hapten-carrier protein) coated strips/microtiter plates (5) Wash solution (6) Substrate(s).

(7) Stopping reagent (optional if end point mode is used; for "rate" mode there is no need of a stopping reagent.

The present invention also provides test kits which are based on an immunoassay (e.g., the ELISA test) for the immunological detection of SAM which contain in addition to antibody against S-adenosylmethionine, for example, the following components:

(a) secondary Ab attached to solid phase;

(b) immobilized hapten, hapten derivatiave, immunogen or alike;

(c) enzyme substrate(s) in solid or dissolved form;

(d) labeled hapten or derivatives (tracer or enzyme conjugates);

(e) buffering and washing solutions;

(f) additives to prevent, for example, nonspecific adsorption and aggregation; and (g) pipettes, incubation vessels, reference standards, calibration curves, and color tables.

The reagent means of the present invention comprises all of the essential chemical elements required to conduct a desired S-adenosylmethionine immunoassay method encompassed by the present invention. The reagent means or system is presented in a commercially packaged form, as a composition or admixture where the compatibility of the reagents will allow, in a test device configuration, or as a test kit, i.e., a packaged combination of one or more containers holding the necessary reagents. Included in the reagent means are the reagents appropriate for the binding reaction system desired, e.g., an antibody and labeled conjugate of the present invention. Of course, the reagent means can include other materials as are known in the art and which may be desirable from a commercial and user standpoint, such as buffers, diluents, standards, and so forth.

In an alternate embodiment, the invention provides a test device comprising the reagent composition and a solid carrier member incorporated therewith. The specific label used in the preferred test kit and test device will depend on the technique followed, as described hereinabove.

In another embodiment, the invention also provides antibodies that specifically recognize SAM. In the past, it has been difficult to raise antibody against SAM using SAM as a hapten because SAM is an unstable molecule. In the present invention, the antibody is therefore raised against a stable analog of SAM. The resulting antibody is specific toward the hapten, obviously; however, since the hapten does not naturally present in the test sample (the biological fluid), this recognition toward the hapten will not cause problem in the assay for determination of SAM. As the hapten is structurally similar to SAM, the resulting antibody cross-reacts with SAM. In the present invention, the antibody raised or selected (monoclonal antibodies) recognizes SAM preferably over SAH (the compound with one methyl group less, and is the precursor for the biosynthesis of SAM as well as the product of transmethylation involving SAM), and other structurally or metabolically related biological compound, such as adenosine. Since SAH always co-exists with SAM, and its concentrations in serum/plasma is at the same range ($10^{-8}$ M, although slight lower than SAM), a SAM antibody that also cross-reacts with SAH substantially will not be very useful in determining the concentration of SAM. Only those antibodies with low cross-reactivity toward SAH can be used in the assay for accurate determination of SAM concentration. In the present invention, the cross-reactivity for compounds such as SAH and adenosine, etc, is less than 10%, preferably, less than 5%, and even more preferably, less than 3%.

The antibodies of the invention which are specific to S-adenosylmethionine and analogs thereof are prepared by inoculating a host animal with an immunogen comprising an immunogenic substance coupled to an S-adenosylmethionine hapten of the formula:

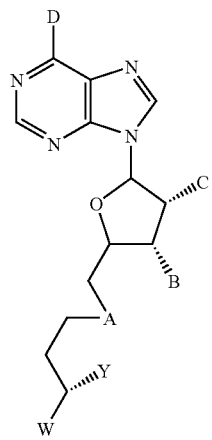

its enantiomers, diastereomers, enantiomerically enriched mixtures, racemic mixtures thereof, isotopically enriched forms thereof, crystalline forms, non-crystalline forms, amorphous forms thereof, charged and non-charged forms thereof, solvates thereof, metabolites thereof, and salts thereof, wherein A is selected from the group consisting of

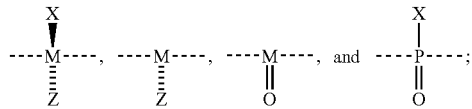

wherein M is selected from the group consisting of N, $N^+$, C, S, $S^+$, Se, $Se^+$, and P; ---- denotes the bonding location for each A group as defined above; X is independently selected from the group consisting of H, $CH_3$, $CH_2OH$, $CH_2NH_2$, OH, $OCH_3$, $NH_2$, SH, CHO, and CN; Z is independently selected from the group consisting of $CH_3$, $CH_2OH$, $CH_2NH_2$, OH, $OCH_3$, $NH_2$, SH, CHO, and CN; B and C are independently selected from the group consisting of H, OH, $NH_2$, SH, F, Cl, Br, and I; D is independently selected from the group consisting of $NH_2$, OH, SH, F, Cl, Br, and I; Y is independently selected from the group consisting of H, $CH_3$, $CH_2OH$, $CH_2NH_2$, OH, $OCH_3$, $NH_2$, SH, CHO, and CN; and W is independently selected from the group consisting of H, COOH, $CONH_2$, $COOCH_3$, CN, CHO and functionalized derivatives thereof; and thereafter collecting serum from said host animal or making monoclonal antibody through fusion, hybridoma selection and cloning process.

In a further embodiment of the invention, there is provided a compound of the formula I

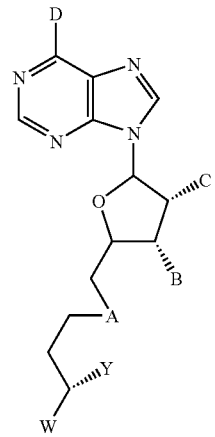

its enantiomers, diastereomers, enantiomerically enriched mixtures, racemic mixtures thereof, isotopically enriched forms thereof, crystalline forms, non-crystalline forms, amorphous forms thereof, charged and non-charged forms thereof, solvates thereof, metabolites thereof, and salts thereof; wherein A is selected from the group consisting of

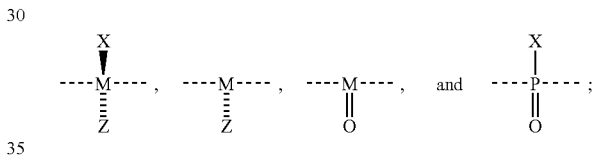

where M is selected from the group consisting of N, $N^+$, C, S, $S^+$, Se, $Se^+$ and P, ---- denotes the bonding location for each A group as defined above; X is independently selected from the group consisting of H, $CH_3$, $CH_2OH$, $CH_2NH_2$, OH, $OCH_3$, $NH_2$, SH, CHO, and CN; Z is independently selected from the group consisting of $CH_3$, $CH_2OH$, $CH_2NH_2$, OH, $OCH_3$, $NH_2$, SH, CHO, and CN; B and C are independently selected from the group consisting of H, OH, $NH_2$, SH, F, Cl, Br, and I; D is independently selected from the group consisting of $NH_2$, OH, SH, F, Cl, Br, and I; Y is independently selected from the group consisting of H, $CH_3$, $CH_2OH$, $CH_2NH_2$, OH, $OCH_3$, $NH_2$, SH, CHO, and CN; and W is independently selected from the group consisting of H, COOH, $CONH_2$, $COOCH_3$, CN, CHO and functionalized derivatives thereof with the proviso that said compound of formula I can not be

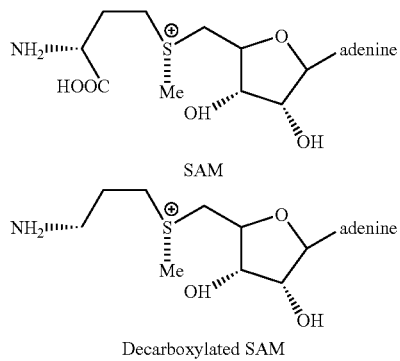

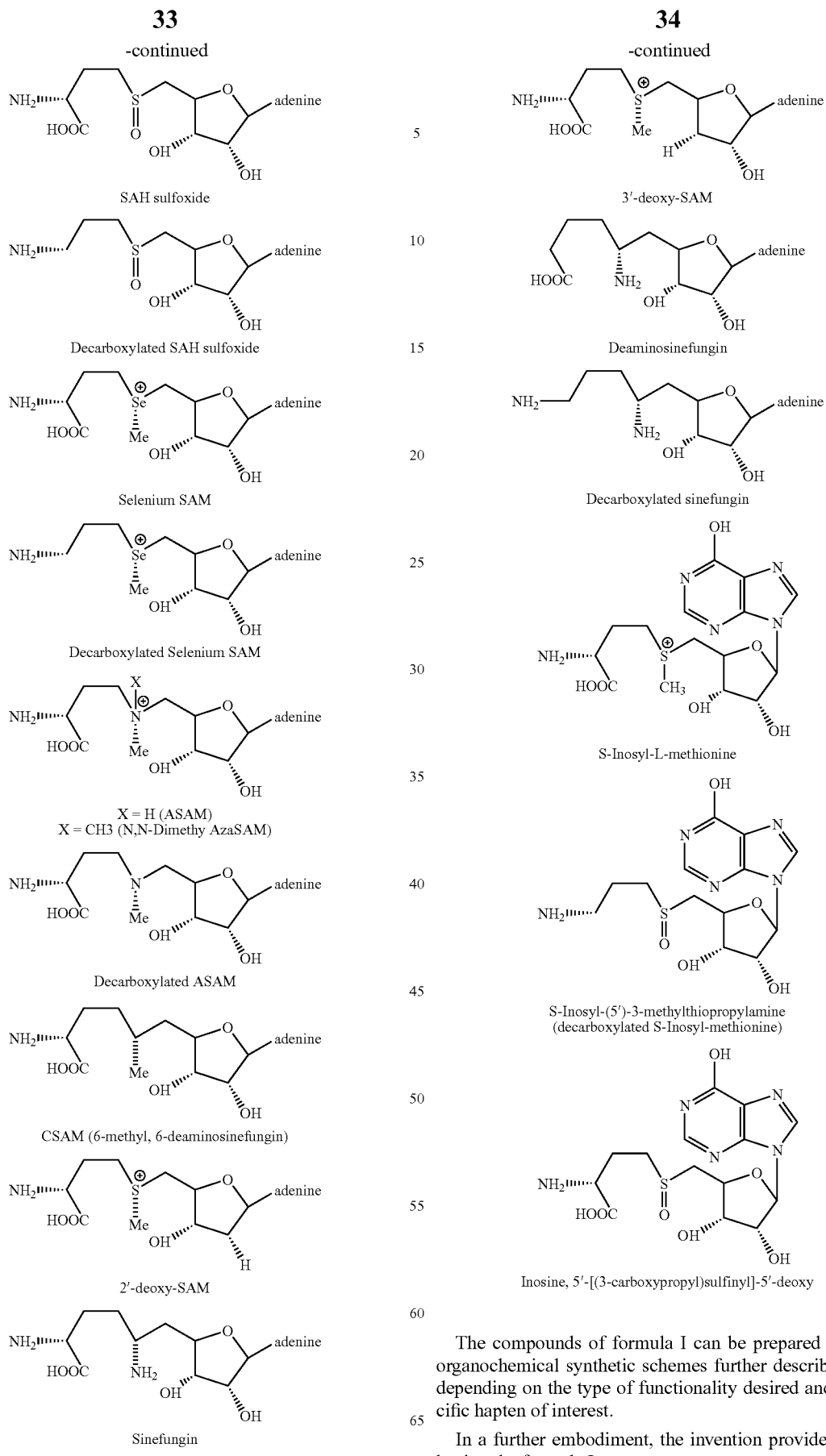
The compounds of formula I can be prepared using the organochemical synthetic schemes further described below depending on the type of functionality desired and the specific hapten of interest.
In a further embodiment, the invention provides haptens having the formula I.

EXAMPLES

The examples which follow are illustrative and are not intended to be limiting of the invention. Unless otherwise indicated, reagents were obtained from commercial sources and, where applicable, were used according to manufacturer's directions.

The following abbreviations are used throughout the examples:

Ab: antibody
AdaM: Azaadenosyl(deamino)methionine
AdaML: AdaM with a linker
Ag: antigen
AP: alkaline phosphatase
ASAM: Aza-SAM, or Nitrogen (N)-adenosylmethionine
BgG: Bovine gamma globulin
BSA: Bovine serum albumin
BTG: Bovine thyrogloblulin
CSAM: Carbon (C)-adenosylmethionine or 6(s)-Methyl-6-deaminosinefungin
daH: Deamino-5-adenosylhomocysteine
daHSO: daH sulfoxide
DCC: N,N'-dicyclohexylcarbodiimide
EDAC: 1-Ethyl 3-(3-Dimethylaminopropyl)carbodiimide
ELISA: enzyme-linked immunosorbant assay
GAM plate/strip: goat-anti-mouse IgG coated microplate or strip
GAR plate/strip: goat-anti-rabbit IgG coated microplate or strip
HRP: horse radish peroxidase
IB: Incubation buffer
KLH: Keho lympet hemocyanine
NHS: N-Hydroxysuccinamide
PBS: phosphate-buffered saline
RT: retention time (for HPLC) or room temperature
SAH: S-Adenosylhomocysteine
SAM: S-Adenosylmethionine
TLC: Thin layer chromatography

Example 1

Preparation of Haptens 1-1. Preparation of 5'-N-Methyl, 5'-N-butyryl-5'-dexoyadenosine (Aza-deamino-SAM, AdaM):

AdaM was prepared by reacting 5'-Methylamino-5'-deoxy-(2',3'-O.O-isopropylidene) adenosine with methyl-4-iodobutyrate followed by base hydrolysis with barium hydroxide to remove methyl ester. The 5'-methylamino-5-deoxy adenosine was prepared from (2',3'-O,O-isopropylidene) adenosine in two steps via 5'-ρ-Toluenesulfonyl-(2',3')-O,O-isopropylidene) adenosine intermediate. (Scheme 1)

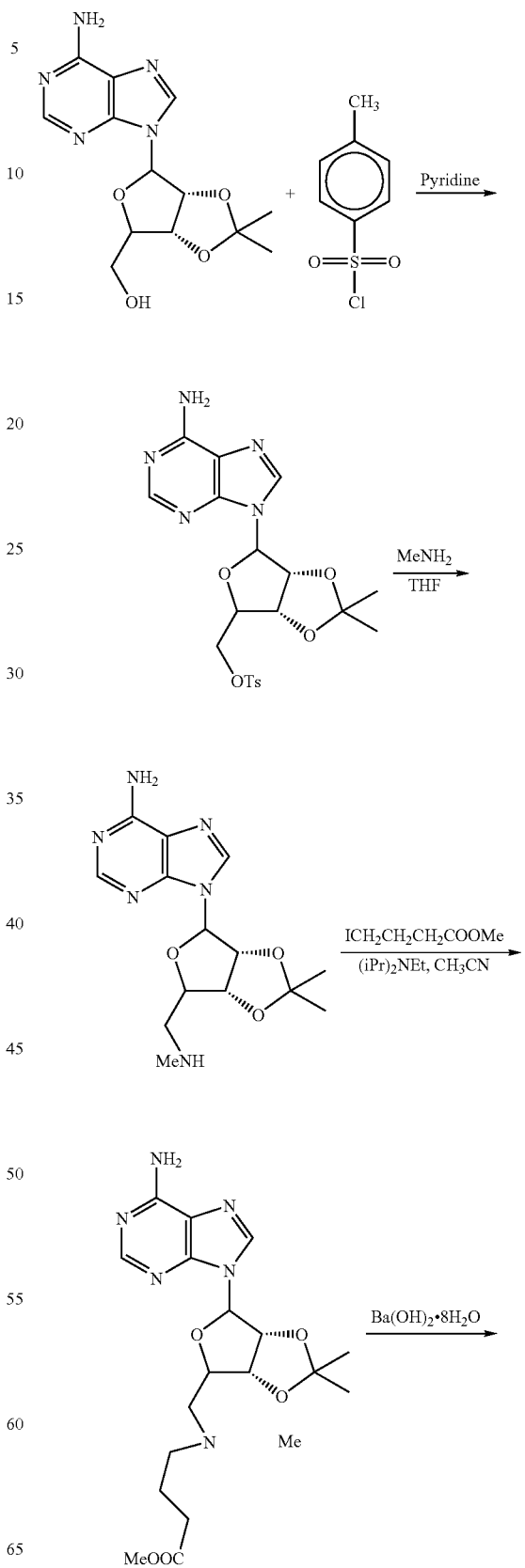

Scheme 1 Preparation of Aza-deamino-SAM (AdaM)

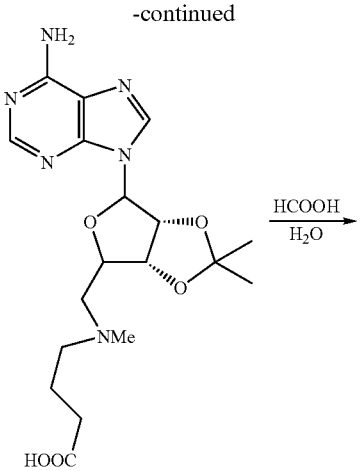

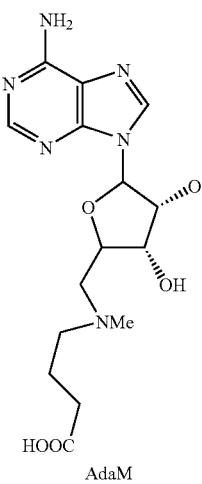

AdaM

5'-ρ-Toluenesulfonyl-(2',3'-O,O-isopropylidene) adenosine: Into a round bottomed flask was added 10 g (32.5 mmole) of (2',3'-O,O-isopropylidene) adenosine followed by 75 ml anhydrous pyridine. The flask was swirled and heated mildly with a heating gun over 15 minutes to aid dissolution of the solids. The solution was cooled with continual stirring in an ice bath, and in five portions a total of 7.1 g (37.0 mmole) of ρ-toluenesulfonyl chloride was added. The reaction mixture becomes light yellow in color. After an hour a 200 μl aliquot was withdrawn to a test tube containing 1 mL of dichloromethane. The mixture was extracted with aqueous sulfuric acid. The organic phase was spotted on tlc (Analtech silica gel, solvent: ethyl acetate), which indicated reaction was approximately 50% complete. The reaction was allowed to continue for several hr until completion.

To the reaction solution was then added 250 mL dichloromethane, and the mixture was first washed with 75 mL of 6N sulfuric acid three times then with 200 mL of water 3 times. The organic phase was then dried over magnesium sulfate. Upon filtration the filtrate was concentrated with a rotary evaporator. The residue was then dissolved in 40 mL dichloromethane, and 250 mL hexane was added to precipitate the product. The solid was further rinsed with hexane, air dried initially, then under vacuum, yield 138.8 g (93%) product. HPLC (Supelco Accentis™ RP-amide column, 25 cm×4.6 mm, 5 μm. Mobile phase: 75% 50 mM ammonium formiate, pH 4.0 and 25% acetonitrile) retention time (RT) at 6.40 min, purity 98%.

5'-Methylamino-5'-deoxy-(2',3'-O,O-isopropylidene) adenosine: Six grams of the above protected 5'-O-tosylate of adenosine was treated with 50 mL of 2.0 M methylamine in THF in a Type Ace pressure tube (20.3 cm length) at room temperature for 4 days, and tlc (silica gel GF, solvent: 30% methanol in dichloromethane; ninhydrin spray was used to identify the amine product.) indicated the reaction was almost complete. The remaining methylamine was removed by passing a stream of argon through the solution. The solution was then rotary evaporated under reduced pressure. The residue was taken up into ethyl acetate and washed with water. After separation, the organic phase was dried over magnesium sulfate. Upon filtration, the filtrate was concentrated to dryness. Preparative TLC (solvent: methanol:ammonium hydroxide:ethyl acetate:hexanae=5:1:8:6) was carried out, and the band containing the methylamino product was isolated, the silica gel grounded, and eluted with a solution of methanol:dichloromethane=3:7 containing a small amount (1-2%) of ammonium hydroxide. Upon rotary evaporation 3.8 grams of white solid (86% yield) was obtained. HPLC (Supelco Accentis™ RP-amide column, 25 cm×4.6 mm, 5 μm. Mobile phase: 75% 50 mM ammonium formate, pH 4.0 and 25% acetonitrile) RT at 5.93 min, purity >94%.

5'-Methylamino, 5'-N-methylbutyryl-5'-deoxy-(2',3'-O,O-isopropylidene) adenosine: Under nitrogen atmosphere to a dry round bottomed flask was added 5 mL dry acetonitrile. To the solution was added the above 5'-Methylamino-5'deoxy-(2,'3'-O,O-isopropylidene) adenosine (258.4 mg, 0.81 mmole) followed by 250 mg (1.1 mmole) of iodomethylbutyrate, and 183 μL of N,N-diisopropylethylamine (1.1 mmole). The mixture was allowed to stir at room temperature for 4 days. The reaction mixture was evaporated to dryness under reduced pressure.

A silica gel (60-200 mesh) column (1.3 cm O.D.×28 cm length) was packed in 10% methanol/$CH_2Cl_2$. Dissolve the reaction mixture residue in 3 ml of 10% methanol/$CH_2Cl_2$ and applied the solution onto the column. Rinse the round bottom flask twice each time with a small amount of the same solvent and applied the rinses to the column. Elude the column with 10% methanol/$CH_2Cl_2$, and fraction of 2 ml volume was collected. Fractions containing the product (Rf=0.25 on TLC, solvent: 10% methanol/$CH_2Cl_2$) were pooled and then evaporated to dryness. A total of 309.7 mg of a slight tan reside was obtained. HPLC (Supelco Accentis™ RP-amide column, 25 cm×4.6 mm, 5 μm. Mobile phase: 80% 50 mM ammonium formate, pH 4.0 and 20% acetonitrile) RT at 10.98 min, purity 93.7%.

5'-N-Methyl, 5'-N-butyryl-5'-deoxy-(2'3'-O,O-isopropylidene) adenosine: Suspend 144 mg of barium hydroxide $8H_2O$ (0.46 mmole) in 24 mL deionized water (DI water). To the milky solution was then added a solution of 127.4 mg (0.3 mmole) of the above methyl butyric ester in methanol/acetonitrile/$CH_2Cl_2$). A biphasic solution was formed with a slightly dark droplet of $CH_2Cl_2$ at the bottom of the mixture. Vigorous stir the mixture at RT and monitor the hydrolysis of the ester by TLC.

After 2 days the reaction mixture was rotary evaporated to dryness. Resuspend the residue in a mixture of 10 mL MeOH and 20 mL $H_2O$. A small stream of carbon dioxide (released from dry ice at room temperature.) was then bubbled into the suspension for 3 hr while stirring. The $CO_2$ saturated solution was then sealed and placed in refrigerator overnight.

Upon filtration through a Whitman filter paper No. 1 the solution was rotary evaporated to dryness. A slight brown viscous residue was obtained, which upon further drying on vacuum line yielded 152.2 mg of a solid paste. HPLC (Supelco Accentis™ RP-amide column, 25 cm×4.6 mm, 5 μm. Mobile phase: 80% 50 mM ammonium formate, pH 4.0 and 20% acetonitrile)) indicated a peak at RT=8.10 min, 97.4% purity)

5'-N-Methyl, 5'-N-butyryl-5'-deoxyadenosine (Aza-deamino-SAM, AdaM): Remove 89.5 mg of the 5'-N-Methyl, 5'-N-butyryl-2'3'-isppropylidenyl adenosine obtained as described above in a small round bottom flask. To the flask was first added 1 mL of DI water, then followed with 1.5 mL of formic acid. The mixture was vigorously stirred at RT overnight. HPLC (same condition as described earlier) of an aliquot indicated the presence of the product at RT=4.80 min, approximately 84% purity.) The mixture was rotary evaporated to near dryness, and a couple drops of formic acid was added to the residue. After stirring for a few more minutes, the mixture was again rotary evaporated to dryness under reduced pressure.

Dowex 50W-X8 (H+ form) cation exchange resin was hydrated, and then washed several times in DI water. A column of 1.6 cm O.D.×24 cm length was then packed. The flow rate was adjusted to a slow 17-18 sec/drop.

The reaction residue was dissolved in a couple milliliter of water, adjusted the pH to acid with 80 μl of 1N HCl, and applied onto the top of the column. Rinse the flask with additional 1 mL×2) DI water and added to top of the column. The column was washed with DI water until the wash from the column was no longer acidic (indicated by pH paper). Elution was then followed with 1 N NH$_4$OH. Fraction of approximately 3.5 ml was collected Fractions containing the product (RT=4.80 min on the HPLC) was then pooled and rotary evaporated to dryness. Upon further drying, a total of 62.3 mg of AdaM was obtained, HPLC indicated >98% purity.

Proton NMR (300 MHz, MeOH-d$_4$) δ 8.26 (s, 1H). 8.23 (s, 1H), 6.01 (d, 1H, J=4.5 Hz), 4.80 (t, 1H, J=4.4 Hz), 4.38 (d, 2H, J=5.4 Hz), 3.50 (t, 1H, J=11.2 Hz), 3.37 (s, 1H), 3.05 (t, 2H, J=6.6 Hz), 2.74 (s, 3H), 2.32 (t, 2 H, J=5.5 Hz), 1.88, (t, 1H, J=6.5 Hz), 1.86 (t, 1H, 6.5 Hz)

1-2. Preparation of AdaML:

The chemistry for putting on a linker to carboxyl group is very straightforward. As an example, trans-4-(aminomethyl)cyclohexanecarboxylic acid was used as a linker. The 4-aminomethylcyclohexanecarboylic acid was first refluxed in dry methanol in the presence of sulfuric acid to form the ester. The 5'-N-Methyl, 5'-N-butyryl-2'3'-isopropylidenyl adenosine was activated to its NHS ester and then conjugated to the amino group of the linker. Removal of the two protecting groups, methyl ester and isopropylidene via base and acid hydrolysis, respectively, gives rise to the AdaML product.

1-3. Preparation of 5'-{[3-(s)-3-Amino-3-carboxylpropyl]-N-methylamino}-5'-deoxy-adenosine (Aza-SAM, ASAM): The preparation of Aza-SAM follows the reported procedure of J. Org. Chem. 1999, 64, 7467-7473 by Mark Thompson, et al. The 5'-Methylamino-5'-deoxy-(2',3'-O,O-isopropylidene) adenosine prepared above and the commercially available N-benzyloxycarbonyl-(s)-glutamic acid were used as starting materials (Scheme 2)

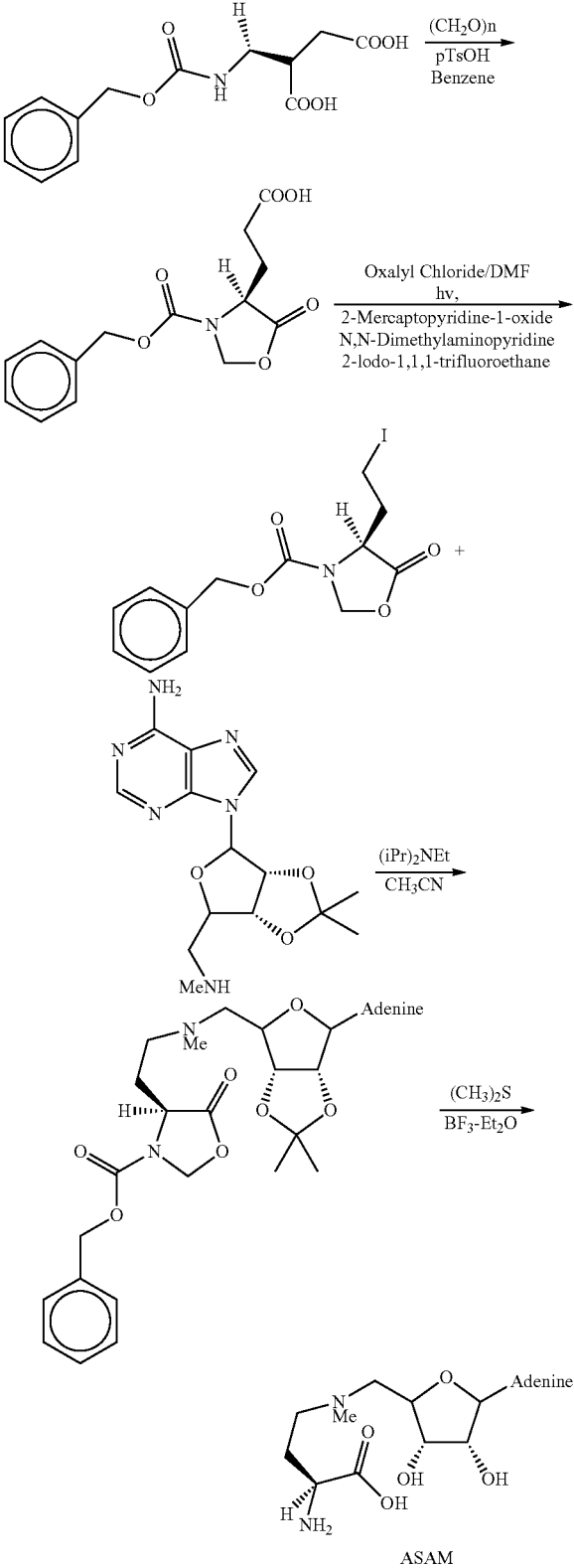

Scheme 2 Preparation of Aza-SAM (ASAM)

(S)-3-Benzyloxycarbony-5-oxo-4-oxazolidine propionic acid: Into a 250 mL round bottomed flask equipped with an Dean-Stark distilling trap was charged 8 g (28.4 mmole) of N-benzyloxycarbonyl-L-glutamic acid, 1.45 g (50 mmole) paraformaldehyde, 28.5 mg p-toluenesulfonic acid monohydrate and 150 mL benzene. The mixture was refluxed for 8 hr during which the solution turned yellowish in color and solid appeared in the condenser and trap. Evaluation with TLC (silica gel GF, solvent: 5% methanol/dichloromethane or ethyl acetate:dichloromethane:acetic acid=1:1:0.05) indicated the reaction was complete. The reaction mixture was cooled down to room temperature, and then rotary evaporated to dryness. The residue was taken into ethyl acetate and washed with benzene. The ethyl acetate solution was dried over magnesium sulfate, filtered, and concentrated to yield the oxazolidine propionic acid product (quantitative recovery)

4 (s)-N-Benzyloxycarbonyl-4-(2-iodoethyl)oxazolidin-5-one: Into a 250 ml three-necked round bottomed flask equipped with a reflux condenser was placed 3.7 g (12.7 mmole) of the above oxazolidin-5-one followed with 125 mL of anhydrous dichloromethane under argon. To the stirring solution was then added 1.16 ml (ca. 1.69 g, 13.3 mmole) of oxalyl chloride and 2 drops of dimethylformamide. The mixture was stirred for 2½ hr and analyzed by TLC (solvent: 10% methanol/dichloromethane). The reaction solution was concentrated with rotary evaporator, and the residue placed under high vacuum.

In another 250 mL three-necked round bottomed flask was placed 1.50 g (10.1 mmole, 1.1 equivalent) of 2-mercaptopyridine-1-oxide, 65 mg (0.53 mmole) of DMAP, 8.6 g (4.05 mL, 41 mmole) of 2-iodo-1,1-trifluoroethane, and 60 mL anhydrous dichloromethane all under argon. The reaction mixture was heated to reflux with an oil bath, and through the side arm in a dropping funnel was added 40 mL dichloromethane containing the above acid chloride over 10 minutes while irradiating with two 100 watt tungsten lamps for additional 1 hr. The mixture was then cooled to room temperature and washed with 50 mL water, followed with a mixture of 25 mL hydrochloride and 50 mL water. The organic phase was separated, dried over magnesium sulfate, and upon filtration the filtrate was concentrated with a rotary evaporator in a water bath without heating. The iodo-compound was purified by flash chromatography.

A silica gel (130 g, 200-400 mesh, 60 Å) column (5 cm O.D.×22 cm length) was wet packed with hexane. The sample was dissolved in 20 mL of a mixture of dichloromethane and hexane (2:1). Elution was carried with 600 mL 2:1 mixture of dichloromethane:hexane, followed with 1500 mL of 5:1 dichloromethane:hexane, and finally 600 ml of dichloromethane. A total of eight 200 mL fractions containing the pure iodo-product (by tlc in dichloromethane) were pooled and then concentrated without heating. Yield was 2.4 g (51%)

Proton NMR (300 MHz, CDCl$_3$) δ 7.38 (s, 5H), 5.56 (s, 1H), 5.28 (d, 1H, J=7.0 Hz Hz), 5.20 (s, 2H), 4.38 (t, 1H, J=5.9 Hz), 3.22 (s, 2H), 2.46 (s, 2H)

4(s)-N-Benzyloxycarbonyl-4-{2-[N-(2',3'-O,O-isopropylidene)-adenosyl-N-methyl]amino-ethyl}oxazolidin-5-one: To a stirring solution of 220 mg (0.584 mmole) of the above iodo-compound in 10 mL of anhydrous dimethylformamide in a round bottomed flask was added 172 mg (0.538 mmole) of the 5'-methylamino-5'deoxy-(2',3'-O,O-isopropylidene) adenosine followed with 104 µL of diisopropylethylamine. The solution was stirred at room temperature for 2 days. TLC analysis on silica gel GF (solvent:10% isopropanol/dichloromethane) revealed a new, more polar material under UV$_{254}$ and iodine stain. The reaction mixture was concentrated on a rotary evaporator under high vacuum. The crude reside was purified by preparative TLC with solvent system of hexane: isopropyanol:dichloromethane=2:1:4. Product band was isolated, extracted from the absorbent with 20% isopropanol in dichloromethane. Upon filtration, the solution was concentrated with a rotary evaporator under reduced pressure. Further drying under high vacuum yielded 155 mg (51% yield) of the desired coupled product. Noted that more material was recovered from the silica gel with the same solvent containing a small amount of ammonium hydroxide, which appeared to open the oxazolidine ring.

Proton NMR (300 MHz, CDCl$_3$) δ 8.38 (s, 1H), 7.95 (s, 1H) 7.36 (broad, s, 5 H), 6.06 (br, 2 peaks, 3H), 5.47 (s, 2H), 5.28 (s. 1H), 5.20 (d, 2H, J=7.0 Hz), 4.89 (s, 1H), 4.35 (br, m, 2H), 2.12-2.59 (m, 9H), 1.62 (s, 3H), 1.39 (s, 3H)

5'-{[3-(s)-3-Amino-3-carboxylpropyl]-N-methylamino}-5'-deoxy-adenosine (aza-SAM, ASAM): To 50 mg (0.088 mmole) of the above protected ASAM in a round bottomed flask was added 4 mL of anhydrous dichloromethane, 110 µL (125 mg, 0.088 mmole) boron trifluoride diethyletherate-, and 165 mg (2.64 mmole) dimethylsulfide. The reaction was monitored by TLC (isopropanol:hexane:dichloromethane=2:3:5) and after 30 minutes no starting material was found. Allow the reaction to continue for 24 hr. A stream of argon was then passed through the solution to remove the solvents. To the residue was then added methanol (3×10 mL) to co-evaporate. The crude product was purified on a preparative TLC plate.

The residue was dissolved in methanol and applied onto the silica gel plate. Upon drying the chromatography was developed in a solvent system with water:70% ethanol:ammonium hydroxide=20:70:4. The product, moved just above the baseline, was then isolated and eluted from absorbent with a mixture of methanol:dichloromethane:ammonium hydroxide=60:40:2. The filtrate was then concentrated with a rotary evaporator, and further dried under high vacuum. Final purification was carried out with Dowex 50W X4 (100 mesh) cation exchange resin column (1.0 cm O.D.×10 cm length). After washing with water until pH is neutral, ASAM was eluted with 0.5 N ammonium hydroxide from the column. Fractions containing the product were pooled, and upon removal of the solvent and under high vacuum, 20 mg (59% yield) of an off-white material was obtained.

Proton NMR (300 MHz, MeOH-d$_4$) δ 8.31 (s, 1H), 8.28 (s, 1H), 6.06 (d, 1H, J=5.1 Hz), 4.54 (m, 1H), 4.40 (t, 1H, J=4.8 Hz), 3.35-3.83 (m, 5 H), 2.90 (S, 3H), 2.18-2.44 (m, 2H). Proton signal for 4'-CH of ribose is buried underneath solvent (OH of methanol) signal due to line broadening. In D$_2$O, δ 8.14 (s, 1H), 8.11 (s, 1H), 5.95 (d, 1H, J=5.3 Hz), 4.90 (br, s, 1H), 4.44 (d, 1H, J=7.9 Hz), 4.30 (t, 1H, J=4.0 Hz), 3.1-3.8 (m, 5 H), 2.80 (s, 3H), 2.22 (m, 1H), 2.12 (m, 1H)

1-4. Preparation of CSAM:

The preparation of CSAM has been reported in J. Org. Chem. 1994, 59, 4186-4193 by Patricia Peterli-Roth et al.

1-5. Preparation of Sinefungin and Analogs:

The preparation of sinefungin, decarboxylated sinefungin, deaminosinefugin, and several other compounds modified at the alkyl side chains have been documented; see, for example, A. K. Ghosh and Y. Wang, J. Chem. Soc., Perkin Trans. I, 1999, 3597-3601; M. P. Maguire, P. L. Feldman and H. Rapoport, J. Org. Chem. 1990, 55, 948-955; P. Blanchard et al, J. Med. Chem. 1991, 34(9):2798-2803; and E. J. Maria et al, Eur. J. Org. Chem 2000, 627-631.

1-6. Preparation of SAM and Selenium-SAM and Analogs:

Organic synthesis and biosynthesis of SAM and SAH are well documented in the literature, so is the synthetic and enzymatic conversion of SAM from SAH. Selenium SAM has been reported (S. H. Mudd and G. L. Cantoni, Nature (London), 180, 1052, 1957). Preparation of SAM Analogs with modified amino acid side chains can be prepared using suitable starting materials and followed these literature procedures.

1.7. Preparation of Deamino-5-Adenosylhomocysteine Sulfoxide, or daHSO: The preparation of deamino-5-adenosylhomocystein sulfoxide can be accomplished by controlled oxidation of thioether from deamino-5-adenosylhomocystein (daH). The latter has been synthesized via several different procedures. Most recently an efficient synthesis was reported by Marc Pignot et al, in European J. Org. Chem. 2000, 549-555. We adopted the procedure of K. Ramalingam and R. Woodard (J. Org. Chem. 1984, 49, 1291-1293) by reacting the 5'-chloro-5'-deoxynucleoside with the sodium salt of thiobutyric acid which was generated in situ from γ-thiobutyrolactone and sodium hydroxide.

Preparation of 5'-Chloro-5-deoxyadenosine: The procedure of Kiyomi Kikugawa and Motonobu Ichino (Tetrahedron Letters, No. 2, 87-90, 1971) was followed. To a round bottomed flask equipped with a stir bar dropwise added 1.5 mL of thionylchloride to 10 mL of hexamethylphosphoramide in an ice bath. Upon completion allow the mixture to warm up to room temperature. One gram of adenosine (3.74 mmole) was then slowly added to the solution, and as the solid dissolved the solution turned orange in color. Allow the reaction to continue at room temperature overnight.

Pouring the orange reaction mixture into a beaker containing 90 ml water, the solution became opaque. The workup involved cation exchange column chromatography with Dowex 50W X8 resin. One hundred and fifty mL of wet resin was used to pack a column. The opaque reaction mixture was then slowly applied onto the column. The column was then washed with approximately 400 mL of deionized water. The chloroadenosine was eluted from the column with 1N ammonium hydroxide. The fractions containing the product (Rf=0.2 on TLC, 10% methanol/$CH_2Cl_2$ vs. the starting material $R_f$=0.1) were pooled, and concentrated with a rotary evaporator under reduced pressure (Dry ice trap is necessary to capture the ammonium hydroxide). To the oily reside obtained was then added 50-60 mL water, upon swirling the flask, a while needle precipitate appeared. Allow the solution to sit inside the fume hood overnight. The precipitate was then filtered, use ice cold water to rinse, and allow the solid to air dry for 2 days. Transfer the chloroadenosine to a glass container and upon vacuum drying a total of 724 mg (70% yield) was obtained.

Preparation of deamino-5-adenosylhomocystein, or daH: The guidance procedure from Biotechology and Applied Biochemistry 9, 39-52, 1987 by Jose Matos, et al was adopted to prepare the deamino-5-adenosylhomocysteine. In a round bottomed flask equipped with a condenser was placed 63.5 mg (0.22 mmole) of the chloroadenosine, 3 mL acetone and then 41.4 mg (0.24 mmole, 1.1 equivalent) of potassium iodide. The mixture was then heated in an oil bath to reflux for 1 hr when some white precipitate appeared on the wall of the flask. Upon cooling, the solution was filtered and the solution concentrated to dryness, presumably chloroadenosine has converted to iodoadenosine.

Under nitrogen atmosphere to a three-necked round bottomed flask equipped with a condenser and an additional funnel was added 201 µl of γ-thiobutyrolactone followed with 70 µl of 10N sodium hydroxide. The generation of mercaptobutyric acid can be detected with dithionitrobenzoic acid (DTNB) in 100 mM Tris buffer.

Dissolve the iodoadenosine in approx. 10 ml THF, and dropwise added to the flask containing the above generated sodium thiobutyric acid solution under nitrogen. The mixture was then heated to 78° C. for 4 hr during which continual monitored with HPLC. The reaction appeared not yet reach completion while competition reaction or degradation of the reaction product became problematic. Upon cooling the reaction mixture was concentrated under reduced pressure and then purified by preparative TLC ($R_f$=0.55-0.65, solvent: ethanol:ammonium hydroxide:water=80:4:16) The product band was isolated, and extracted with methanol. Upon drying over sodium sulfate, the methanol solution was filtered and concentrated to dryness. The yield was ≦30%. MS: m/e+ 1370

Preparation of daH sulfoxide, daHDO: dah sulfoxide can be prepared by treatment of daH with $H_2O_2$ (C. Wise and F. Fullerton, Journal of Liquid Chromatography, 18 (10), 2005-2017, 1995), or with sodium metaperiodate. (J. C. Martin and J. J. Uebel, Am. Soc., 86, 2936, 1964; C. R. Johnson and D. McCants, Am. Soc., 86, 2935, 1964) Conversion of sulfide to sulfoxides in water has also been reported using hypervalent iodine reagents recently (H. Tohma et al, ARKIVOC 2003 (vi) 62-70)

1-8. Preparation of P-Chiral Phosphine and Phosphine Oxide Derivatives of SAM: Classical synthesis of P-chiral triorganophosphines involved successive substitution of $PX_3$ (X=halogen, OR) by Grignard- or organolithium reagents (G. M. Kosolapoff and L. Maier, Organic Phosphorous Compounds, Wiley-Interscience, New York, 1972.) Alternatively, construction of P—C bond can be achieved by hydrophosphination, an addition process of P—H function of phosphine to alkenes (W. Wolfsberger, Chem Ztg. 112: 53, 1988). Hydrophosphination with the cationic primary phosphine iron complexes was reported to offer stereocontrol and suitable for further derivatization (W. Malishch, et al, J. Organometallic Chemistry 661: 95-110, 2002). Release of the phosphines from the metal is achieved by photoinduced ligand exchange. Phosphines can then be readily oxidized to phosphine oxides in air or by oxidants.

1-9. Preparation of SAM Analogs with Modified Adenine at 6-Amino Position: This group of hapten can be synthesized by using modified adenosine as starting material then following the construction rationale and schemes outlined in the current invention as well as cited literatures. Inosine (6-hydroxy instead of 6-amino), 6-mercaptonpurine-9-β-D-ribofurnoside, and a halogen at 6 position such as 6-chloropurineriboside are all commercially available compounds.

1-10. Preparation of Sugar-Modified SAM Analogs: Modification at the ribose moiety (replacing 2'- and/or 3'-hydroxyl groups) of the SAH has been reported. One example is A Synthesis of Sugar-modified S-adenosyl-L-homocystien (AdoHcy) Analogues as Inhibitors of AdoHcy Hydrolase by B-T Kim, Bull. Korean Chem. Soc. 2005, 26(1) 171-174. The chemistry utilized in the paper and its references can be adopted for the synthesis of sugar-modified SAM analogs described in this invention.

Example 2

Preparation of Conjugates 2-1. General Procedure:

Review on protein conjugation is readily available (Bioconjugation Techniques, by Hermanson, G. T., Academic Press Inc., 1995; Chemistry of Protein Conjugation and Cross-Linking, by Wong, S. S., CRC Press, Inc. 1991; Crossinking Reagents, technical handbook, Pierce Biotechnolgoy, Inc. 2005). Technical handbooks and bulletins from commercial sources are abundant. The description that follows are a few common examples of conjugation chemistries which are readily available to someone of ordinary skill in the art.

A hapten with a carboxyl functional group was reacted with NHS in the presence of DCC in DMF. The NHS ester of the hapten in DMF was then slowly added to a solution of protein in 100 mM phosphate (pH 8.0), or 100 mM carbonate or bicarbonate (pH 9.0). For immunogen, the carrier protein can be BSA, BgG, BTG, or KLH, etc. while for enzyme conjugate, the enzyme with high specific activity, e.g., HRP, AP, and β-galactosidase, etc.

A compound with amino group can be directed linked to carboxyl groups of the protein with EDAC. It can also first be converted to carboxyl containing molecule by reacting with succinic anhydride or similar compound, then conjugate to protein following the procedure described above. It can also react with a hetero-bifunctinal linking agent (cross-linking) such as N-(a-maleimidoacetoxy)-succinimide ester and introduce a SH functional group upon removal of acetoxyl group. Molecule containing sulfhydryl group can be then linked with sulfhydryl group or amino group of the protein readily.

The conjugate was then worked up via a sephadex gel filtration column in PBS to remove excess reagents or small molecules of byproducts. When necessary dialysis was carried out to further remove any contamination of small molecules.

For illustration, the procedure for the preparation of immunogen AdaM-BSA and enzyme conjugate AdaM-HRP were performed as follows:

2-2. Preparation of AdaM-NHS: To a flask containing overnight vacuum-died AdaM (15.8 mg, ca. 0.043 mmole) was added 22.0 mg (0.107 mmole) of DCC and 7.2 mg (0.063 mmole) NHS. The solid mass was left on vacuum line for 3-4 hr drying. Approximately 1.5 mL dry DMF was then added to the flask under nitrogen atmosphere, and then seal the flask. The solution was stirred at RT overnight. TLC (10% MeOH in $CH_2Cl_2$) analysis indicated the formation of NiS ester.

2-3. Preparation of AdaM-BSA: Weight out 62.1 mg (ca. $9.6 \times 10^{-4}$ mmole) BSA to a round bottomed flask and added 5 mL freshly prepared 100 mM sodium phosphate solution, pH 8.25. Place the BSA solution in a 4° C. water bath with vigorous stirring. The AdaM-NHS prepared as described above was then slowly added in 10 ul aliquot every few minutes. After a total of 150 ul was added, the conjugation mixture became turning cloudy. One milliliter of DMSO solution was added to aid dissolution. Upon addition of another 50 ul AdaM-NHS in DMF, the mixture turned cloudy again. Water bath sonication was then applied for 5 minutes after every 10 uL×5 of AdaM-NHS was added. At the conclusion of 900 ul in total of AdaM-NHS in DMF was added, the mixture was sonicated for 20 minutes.

A Sephadex G25 column (1.8 cm OD×21.5 cm length) was equilibrated with PBS (pH 7.0). The reaction mixture was carefully applied onto the column. AdaM-BSA conjugate was then separated from excess reagents and small molecule byproducts with PBS elution. Fraction of ca. 3.5 mL was collected. Conjugate fractions (#3-8) were identified by $OD_{260}$ absorption, and then pooled. To insure the conjugate was free from any hapten, the pool was dialysis against PBS (1.5 liter×4) over 2 days. The final volume of the conjugate is approx. 29.5 ml, at estimated 2.0 mg/ml BSA.

2-4. Preparation of AdaM-HRP: The procedure for HRP conjugation is similar to that of AdaM-BSA. Weight out 15 mg HRP powder (Toyobo Enzymes, PEO-131, Shinko American Inc, New York, N.Y.) and dissolve it in 2 ml 100 mM sodium bicarbonate buffer, pH. 8.96, in a round bottomed flask.

Ten microliter (10 uL) aliquot of AdaM-NHS in DMF was then added slowly. Upon addition of a total of 200 uL of the NHS the reaction mixture was worked up via Sephadex G25 column. Fractions containing the HRP conjugate were then pooled, and further dialyzed with PBS (1.5 liter×4) over 2-3 days. Total volume of conjugate was 5.8 mL, and estimated concentration of HRP based on $OD_{402}$ was 1.7 mg/mL.

Example 3

Antibody Preparation 3-1. General Procedure:

The examples below are illustrative of the invention, and not intended to be limiting. Various animals such as mouse, rat, goat, sheep, and chicken, etc. can be used to produce polyclonal antibody. Once the polyclonal production is successful, monoclonal production becomes feasible. Mouse monoclonal production is a common practice, based on the procedure developed by the pioneer work of Kolher and Milstern (Nature, 256, 495-497, 1975). Rabbit monoclonal and Rabbit-Mouse hybrid monoclonal clones have been demonstrated more recently (Stronsberg, A. D. and Guillet, J-G., U.S. Pat. No. 4,859,595, 1989; Raybould, T. J. G., and Takahashi, M. U.S. Pat. No. 4,977,081, 1990; McCormack, R. T. et al, U.S. Pat. No. 5,472,868, 1995; Spieker-Polet, et al, PNAS 92, 9348-9524, 1995.)

Blood was collected periodically from immunized animals and cells were removed by centrifugation. Antisera thus obtained were then evaluated to determine the immune response and the antibody titer. Depending on application, antibody may be used directly. When necessary, they can be further purified to immunoglobulin level with ammonium sulfate or sodium sulfate or by protein A column chromatography, etc.

For monoclonal antibody, once the clone is obtained it can be injected into host for ascite production. Antibody was then purified from the ascite fluids by protein A affinity column. The hybridoma clone can also be cultured on hollow fiber method to produce antibody.

Depending on special requirements or needs of application, monoclonal antibody thus obtained may be further processed while retaining its specificity, to fragments such as fab, fab', and $(fab')_2$, Fc etc., or utilized as part of a chimeric antibody, or humanized, or genetically engineered, etc.

3-2. Rabbit Polyclonal Antiserum

New Zealand White rabbits were used for polyclonal antibody production. Immunization (1 ml total volume) was carried out with subcutaneous injections at multiple sites. Initial injection utilizes 1:1 mixture of complete Freund Adjuvant and AdaM-BSA conjugate solution in PBS upon emulsification. Subsequent injections use incomplete Freund adjuvant. The immunization was on 21 days cycle schedule, the animals were bleed from the ear artery (rabbit sedated) between 7 to 14 days after injection, normally on the $10^{th}$ day. The blood was then processed to serum via centrifugation to remove red blood cells and clots. Immune response was detected after three booster injections. See FIG. 1 for a typical positive antibody response (indicated by antibody titer determination) wherein NA005 and 006 are animal designation numbers, 0 represents pre-bleed, 1 represents the first bleed after 4 immunizations.

3-3. Mouse Polyclonal Antiserum

BALB/c mice were used for the polyclonal program. Immunization procedure is similar to that described in the rabbit program except the volume of injection is at 0.2 ml at multiple sites. The schedule for immunization and bleeding are also the same as the rabbit program. The bleed was tapped from the tail of the mouse. The amount of serum can be obtained from mice is very limited. Nevertheless, it is sufficient and necessary for evaluation before going forward with fusion to generate mouse monoclonal antibody.

3-4. Mouse Monoclonal Antibodies

Mouse that responded well with immunization was primed with IV injection of immunogen one and three days prior to its termination. The spleen of the mouse was harvested and homogenized with a French Press. The spleen cells were then fused with myeloma NS-1 cells in 4:1 ratio. The fused cell suspension was then plated out on 96 wells microtiter plates.

8. Read $OD_{450}$ on a Perkin Elmer Lambda (microtiter plate) Reader.

Results: (See Table 1 below)

TABLE 1

| [SAM] | $OD_{450}$ | stdev | [SAH] | $OD_{450}$ | stdev | [Adenosine] | $OD_{450}$ | stdev | [Guanosine] | $OD_{450}$ | Stdev |
|---|---|---|---|---|---|---|---|---|---|---|---|
| 0 | 0.310* | 0.007 | 0 | 0.331* | 0.015 | 0 | 0.364 | 0.015 | 0 | 0.406 | 0.011 |
| 1.4E−9 | 0.321 | 0.008 | 1.4E−8 | 0.337 | 0.001 | 5.6E−9 | 0.342 | 0.003 | 3.0E−9 | 0.350 | 0.009 |
| 1.4E−8 | 0.304 | 0.003 | 1.4E−7 | 0.323 | 0.006 | 5.6E−8 | 0.339 | 0.002 | 3.0E−8 | 0.324 | 0.019 |
| 1.4E−7 | 0.252 | 0.008 | 1.4E−6 | 0.293 | 0.005 | 5.6E−7 | 0.305 | 0.006 | 3.0E−7 | 0.374 | 0.015 |
| 1.4E−6 | 0.192 | 0.004 | 1.4E−5 | 0.244 | 0.005 | 5.6E−6 | 0.300 | 0.010 | 3.0E−6 | 0.383 | 0.016 |
| 1.7E−5 | 0.153 | 0.004 | 1.4E−4 | 0.209 | 0.006 | 5.6E−5 | 0.256 | 0.005 | 3.0E−5 | 0.371 | 0.016 |

*By error the 0.2% BSA buffer (instead of 0.5% BSA buffer) was used as zero samples in the SAM and SAH cases.

The hybridoma were grown on Eagle Medium enriched with fetal bovine serum, sodium pyryvate, MEM/NEAA, HT supplement, aminopterine, and penicillin-streptomycin mixture and screened. Clones that are positives to AdaM-HRP conjugate were selected for further studies. Final selection was based on assay performance and cross activity profile. Selected clones were then injected into mice to produce ascite fluid.

Example 4

4-1. Assay 1 Assay (End Point) with Rabbit Antibody and Antibody Specificity
Reagents:
1. Goat anti-rabbit coated microtiter well strips.
2. —Rabbit antiserum diluted in incubation buffer (IB: 10 mM phosphate, 150 mM NaCl, 0.2% BSA, 0.1% Tween 20, 0.1% Proclin, pH 7.4)
3. An IB+Tris (100 mM) buffer, pH 8.5
4. Samples:
   (a) SAMe toluenesulfonate (tosylate) disulfate at concentration from $1.4 \times 10^{-5}$-$^9$ to $1.4 \times 10^{-5}$ M in IB containing BSA 0.5%, and use 0.5% BSA-IB as zero sample.
   (b) SAH at concentration from zero and $1.4 \times 10^{-8}$ to $1.4 \times 10^{-4}$ M.
   (c) Adenosine at concentration from zero and $5.6 \times 10^{-9}$ M. to $5.6 \times 10^{-5}$ M
   (d) Guanosine at concentration from zero and $3.0 \times 10^{-9}$ M to $3.0 \times 10^{-5}$ M
5. AdaM-HRP conjugate (diluted to HRP concentration @30 μg/mL) in IB.
6. —HRP substrate: one reagent substrate solution NeA-blue Tetramethylbenzidine Substrate, Clinical Science Products, Inc., Mansfield, Mass.
7. 1N phosphoric acid Procedure:
1. —The rabbit antiserum was diluted 1:12,500 in IB and pre-incubated (60 μl/well) in goat-antirabbit coated strips for at least one hour.
2. Excess antibody was then decanted, washed, and blot dry.
3. To each well was then added 10 μl of the pH 8.5 IB+Tris buffer followed by 25 μl of samples. The mixture was incubated on a orbital shaker for 25 min. All samples were tested in duplicate except the zero sample, in 6 wells.
4. Twenty five microliter (25 μl) of AdaM-HRP conjugate solution was then added and incubated for additional 25 min with shaking.
5. The assay mixture was then decanted, washed, and blot dry.
6. To each well was added 60 μl/well of HRP substrate and incubate for 15 min.
7. Stop the substrate development with 120 μl/well of 1N phosphoric acid.

Figure 2:
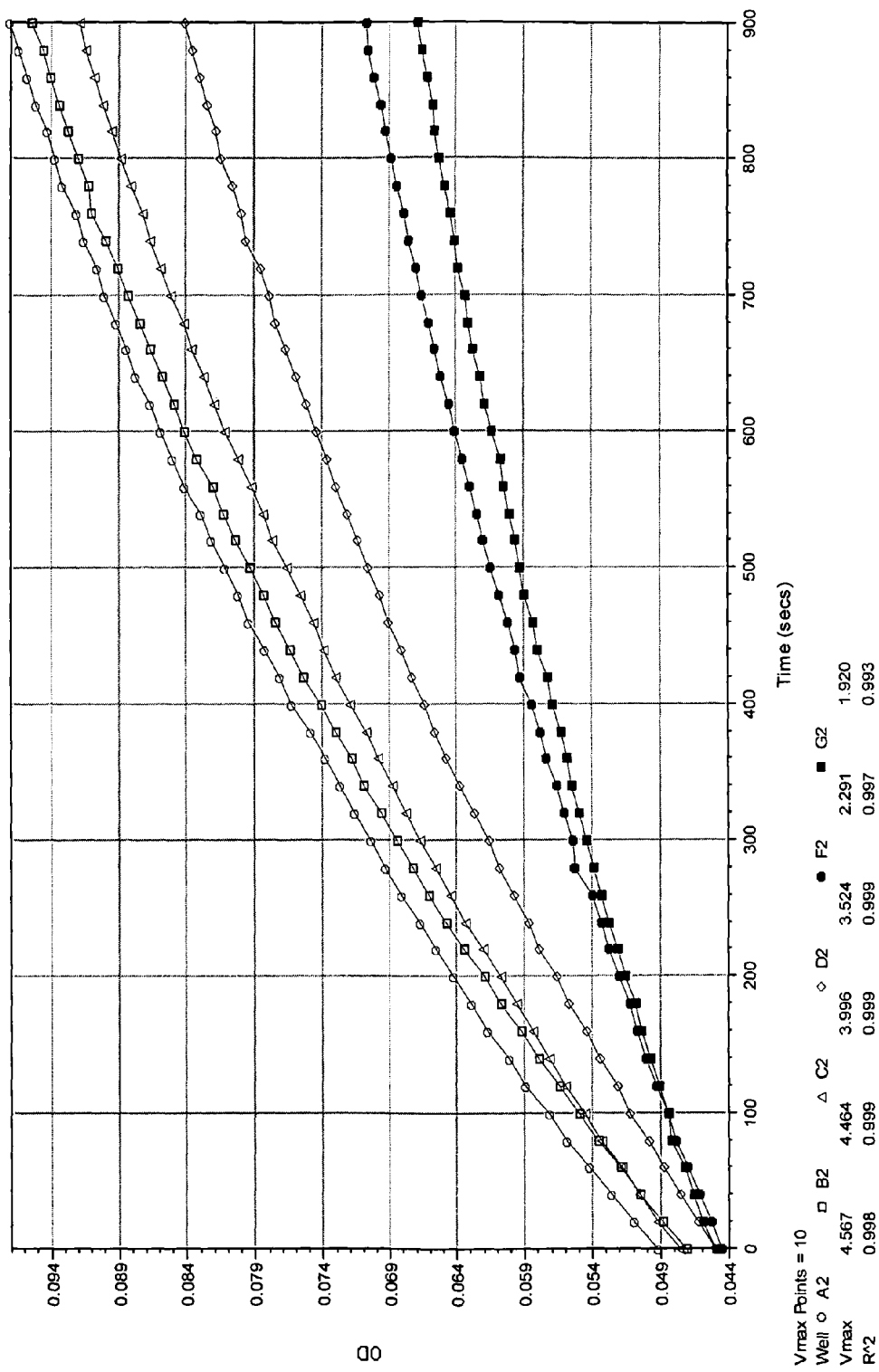
FIG. 2 illustrates the Dose Response in Kinetic Mode (with Rabbit Antibody): The graph illustrates the dose response of SAM in the immunoassay with an anti-SAM antibody. Color development ($OD_{650}$) of TMB substrate was monitored continuously for 15 minutes at 20.7° C. The Vmax in 20 sec interval ($OD_{650}$) was plotted. In ascending order Well A contains zero concentration of SAM, Well G contains the highest concentration of SAM. The detailed procedure for the assay is described in Example 4, Assay 2.

4-2. Assay 2 Assay (Kinetic Mode) with Rabbit Antibody
Reagents: same as above except only SAM was used as sample.
Procedure:
1. The specific antibody was diluted to an appropriate concentration in PBS buffer and pre-incubated (60 μl/well) in goat-antirabbit coated strips for at least one hour.
2. Excess antibody was then decanted, washed, and blot dry.
3. To each well was then added 10 μl of pH 8.5 IB+Tris buffer followed by 25 μl of samples. The mixture was incubated on a orbital shaker for 25 min. All samples were done in duplicate except zero sample was carried out in 6 wells.
4. Twenty five microliter (25 μl) of AdaM-HRP conjugate solution was then added and incubated for additional 25 min with shaking.
5. The assay mixture was then decanted, washed, and blot dry.
6. To each well was added 60 μl/well of HRP substrate and the color development was monitored in kinetic mode on a Molecular Device SpectraMax reader, and $OD_{650}$ was monitored every 20 sec. for 15 min. (A representative graph for the kinetic data is shown in FIG. 2.)
7. Stop the substrate development with 120 μl/well of 1N phosphoric acid.
8. $OD_{450}$ was recorded.

Results: See Table 2 Below. (Average of Replicates)

TABLE 2

| [SAM] (M) | Kinetic Mode (slope, $\Delta OD_{650}$/min) | End Point Mode ($OD_{450}$) |
|---|---|---|
| 0 | 4.293 | 0.2411 |
| 1.4E−9 | 4.324 | 0.2405 |
| 1.4E−8 | 4.015 | 0.2252 |
| 1.4E−7 | 3.568 | 0.2089 |
| 1.4E−6 | 2.395 | 0.1586 |
| 1.4E−5 | 1.860 | 0.1353 |

4-3. Assay 3 Assay with Mouse Antiserum
Reagents:
1. Goat anti-mouse coated microtiter well strips.
2. —Mouse antiserum diluted in incubation buffer (IB: 10 mM phosphate, 150 mM NaCl, 0.2% BSA, 0.1% Tween 20, 0.1% Proclin, pH 7.4)
3. An IB+Tris (100 mM) buffer, pH 8.5
4. Samples: SAMe toluene-sulfonate (tosylate) disulfate at concentration from $5.0 \times 10^{-9}$ to $5.0 \times 10^{-5}$ M in IB, and use the IB as zero sample.
5. AdaM-HRP conjugate (diluted to HRP concentration @30 ug/mL) in the IB.
6. —HRP substrate: one reagent substrate solution NeA-blue Tetramethylbenzidine Substrate, Clinical Science Products, Inc., Mansfield, Mass.
7. 1N phosphoric acid Procedure:
1. The mouse antiserum was diluted 1:15,000 in IB and pre-incubated (60 ul/well) in goat-antimouse coated strips overnight.
2. Excess antibody was then decanted, washed, and blot dry.
3. To each well was then added 10 μl of the pH 8.5 IB+Tris buffer followed by 25 μl of samples. The mixture was incubated on an orbital shaker for 31 min. All samples were done in duplicate except zero sample was carried out in 6 wells.
4. Twenty-five microliter (25 μl) of AdaM-HRP conjugate solution was then added and incubated for additional 35 min with shaking.
5. The assay mixture was then decanted, washed, and blot dry.
6. To each well was added 50 μl/well of HRP substrate and incubate for 15 min.
7. Stop the substrate development with 100 μl/well of 1N phosphoric acid.
8. Read OD-450 on a microplate reader.
Results: (See Table 3 Below)

TABLE 3

Figure 3:
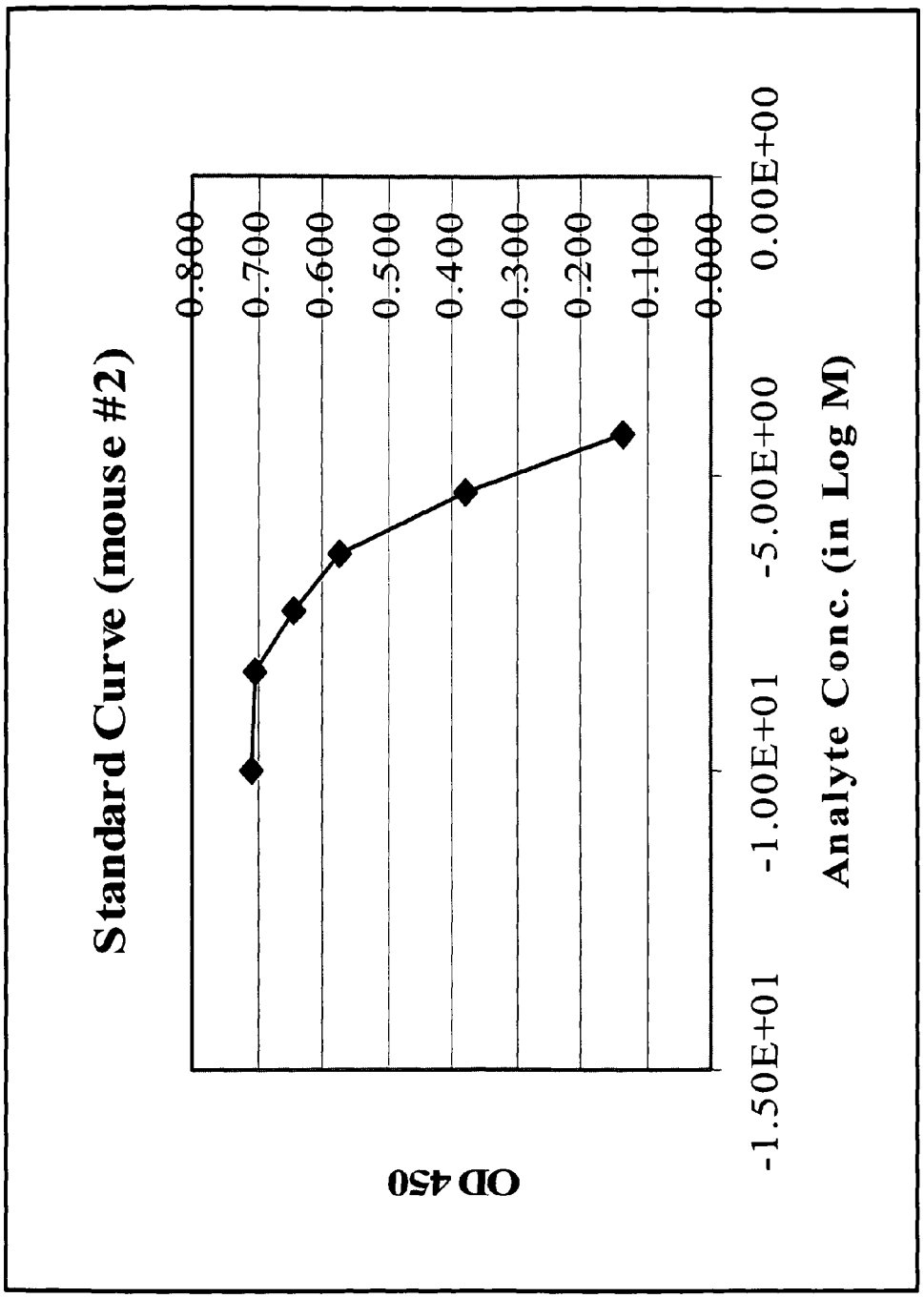
FIG. 3 describes the Dose Response Curve with Mouse Antibody: The graph features an immunoassay (ELISA) for the determination of the concentration of SAM. Procedure for the assay is described in Example 4, Assay 3. The data were averages of duplicates; assay background was not subtracted.

| [SAM] (M) | Log [SAM] | Average $OD_{450}$ |
|---|---|---|
| 0 | Use −11 for graphing (see FIG. 3) | 0.710 |
| $5.0 \times 10^{-9}$ | −8.30 | 0.704 |
| $5.0 \times 10^{-8}$ | −7.30 | 0.642 |
| $5.0 \times 10^{-7}$ | −6.30 | 0.574 |
| $5.0 \times 10^{-6}$ | −5.30 | 0.376 |
| $5.0 \times 10^{-5}$ | −4.30 | 0.137 |

4-4. Assay 4 ELISA Using Antigen-Coated Solid Phase
Reagents:
1. —AdaM-BSA (immunogen) coated microtiter well strips. This was prepared as follows: The immunogen was diluted to 0.05 μg/mL in 100 mM phosphate buffer (pH 8.2). Pipette 60 μl of this solution to each well and incubate overnight at room temperature. Excess reagent was then decanted, the strip washed and blot dry. To each well was then added a blocking solution (300 μl/well) containing 1% BSA in PBS (pH 7.4) and incubate for 1 hr. Upon decant/wash/blot dry the strip is ready to use.
2. —Rabbit antiserum diluted appropriately (1:16,000 in the example) in IB (10 mM phosphate, 150 mM NaCl, 0.2% BSA, 0.1% Tween 20, 0.1% Proclin, pH 7.4)
3. An IB+Tris (100 mM) buffer, pH 8.5
4. Samples:SAMe tosylate disulfate at concentration from zero to $5.0 \times 10^{-5}$ M in IB.
5. —Goat-antirabbit (GAR)—HRP conjugate (Jackson ImmunoResearch Lab., Inc., West Grove, Pa., 111-036-046) diluted 1:30,000 in IB buffer
6. —HRP substrate: one reagent substrate solution NeA-blue Tetramethylbenzidine Substrate from Clinical Science Products, Inc. (Mansfield, Mass.)
7. 1N phosphoric acid
Procedure:
1. Mix 24 μl/well IB+Tris buffer, 60 μl/well sample and 60 μl/well of HRP conjugate to a column of a non-binding microtiter plate or an 8-wells strip. Incubate the mixture on an orbital shaker for 30 minutes at room temperature. All samples were done in duplicate except zero sample was carried out in 6 wells.
2. Transfer 50 μl/well of mixture to the immunogen-coated strips, and incubate for 20 minutes with shaking at RT.
3. The reaction mixtures were then decanted, all wells washed and blot dry.
4. To each well was then added 50 μl of GAR-HRP and incubate for 20 min with shaking.
5. Excess GAR-HRP was then decanted, the wells washed, and blot dry.
6. To each well was added 50 μl/well of HRP substrate and incubate for 7 min.
7. Stop the substrate development with 100 μl/well of 1N phosphoric acid.
8. Read $OD_{450}$ on a Microtiter Plate Reader.
Results: (See Table 4 Below)

TABLE 4

| [SAM] (M) | $OD_{450}$ | % Inhibition* |
|---|---|---|
| 0 | 0.638 | 100.0% |
| $5.0 \times 10^{-9}$ | 0.573 | 89.9% |
| $5.0 \times 10^{-8}$ | 0.491 | 77.0% |
| $5.0 \times 10^{-7}$ | 0.340 | 53.3% |
| $5.0 \times 10^{-6}$ | 0.233 | 36.4% |
| $5.0 \times 10^{-5}$ | 0.204 | 32.0% |

*% Inhibition was calculated without subtraction of background signal.

Example 5

ELISA Kits 5-1. A Typical, Generic ELISA Assay Kit
A common ELISA assay kit includes the following specific components:
(1) a set of calibrators (typically 3-5 vials each contains a different amount of SAM, including zero concentration)
(2) antigen (e.g., AdaM-BSA)-coated solid phase (e.g., breakable microtiter plate well or strip in lockwell frame, or plate.
(3) an anti-SAM antibody in appropriate concentration and optimized pH.
(4) Optional reagents: generic, available in the market. Can be included or provided for convenience to the end user.
(a) an appropriate secondary antibody-HRP conjugate solution (e.g., GAM-HRP if the prime antibody is a mouse antibody) diluted to tens to hundreds ng/ml in concentration in a suitable buffer.
(b) Wash solution,
(c) HRP substrate solution, and
(d) Stopping reagent To each antigen-coated well is added 25 μl sample (a calibrator or a test sample) followed by 25 μl of the antibody solution. After incubation for 15-30 minutes, decant the mixture, wash the well, and remove all liquid by blotting or suction. Fifty microliter of the secondary antibody-HRP conjugate solution is then added, and incubate for ca. 30 minutes, then decant, wash and blot dry (or by suction). HRP substrate solution (such as the aforementioned NeA blue solution) is then added, incubated, and signal measured. For end point assay, a stop reagent is added before signal is read. Based on the standard curve established from the calibrators, the concentration of SAM in the sample can then be determined.

5-2. Another Common, Generic ELISA Assay Kit
The assay kit comprises the following specific reagents:
(1) a set of calibrators (typically 3-5 vials each contains a different amount of SAM, including zero concentration)
(2) a SAM analog-HRP conjugate solution
(3) an anti-SAM antibody solution (4) Optional generic reagents and materials: can be included or provided for convenience to the end user.
  (a) an appropriate secondary antibody-coated microwell, or strip in lockwell frame, or plate,
  (b) Wash solution,
  (c) HRP substrate solution, and
  (d) Stopping reagent To each secondary antibody-coated well is added 50-60 ul of antibody solution, and incubate for at least 1 hr at room temperature. Decant, wash and then blot dry (or by suction). To the well is then added 25 ul sample (a calibrator or a test sample) followed by 25 ul of the SAM analog-HRP conjugate solution. After incubation for 10-30 minutes, decant the mixture, wash the well, and remove all liquid by blotting or suction. Fifty microliter of HRP substrate(s) solution is then added, incubated, and signal measured. For end point assay, a stop reagent is added before signal is read. Based on the standard curve established from the calibrators, the concentration of SAM in the sample can then be determined.

5-3. An ELISA Kit Utilizing Avidin-Biotin Binding Pair
An ELISA kit contains the following reagents:
  (1) a set of calibrators (typically 3-5 vials each contains a different amount of SAM, including zero concentration)
  (2) avidin or streptavidin-coated paramagnetic particles reagent
  (3) a biotin-SAM analog conjugate solution
  (4) a HRP-labeled antibody solution
  (5) optional reagents: Wash solution, HRP substrate solution and stopping reagent.

In a suitable vessel (e.g., test tube) mix a calibrator or a test sample with the biotin-SAM analog conjugate solution followed by the HRP-labeled antibody solution. After incubation for a few minutes the avidin/strepavidin-coated magnetic particles is added to the mixture and vortexed for ca. 10 seconds. Use a magnet (or a magnetic separator such as the Corning magnetic separator or apply magnetic field) to separate the magnetic particles to the side(s) or the bottom of the vessel from the liquid. Upon removal of the liquid phase, the magnet (or equivalent) is removed, and the magnetic particles are washed with a buffer. Apply the magnet to pull particles to the side(s) or bottom of the vessel, and remove the wash by suction or blotting. Repeat the washing process once. Finally, HRP substrate solution is added, the mixture is vortexed. Apply the magnet to remove magnetic particles to the sides or the bottom of the test vessel, and signal in the clear liquid is then measured. Based on the standard curve established from the calibrators, the concentration of SAM in the sample can then be determined.

5-4. Dipstick Format
In a dipstick kit format, a plastic strip is affixed to a vial cap so that it hangs down into a vial. On the surface of the dipstick is a two cm² detection area to which is affixed an appropriate amount of anti-SAM antibody. The sample is diluted into a vial containing a solution of SAM-BSA-biotin conjugate. The vial cap with the dipstick is screwed onto the vial and incubated for approximately 15-30 minutes. The dipstick is removed and rinsed with water or buffer and screwed onto a vial containing an avidin-HRP (horseradish peroxidase) complex, incubated for 15 min, and then rinsed. The dipstick is then placed in a vial containing HRP substrate such as azino-bis-ethylbenzthiazoline sulfonic acid ("ABTS"). SAM concentration is then estimated by determining the intensity of the blue color in the vial after a specified incubation period.

5-5. Membrane Format
The anti-SAM antibody is affixed to a membrane and the membrane (approximately two cm² containing an appropriate amount of antibody) is placed over a small cup. The sample is mixed with the SAM-BSA-biotin conjugate (consisting of a 1:2 dilution of the sample, with appropriate amount of conjugate) and this solution poured over the membrane. Gravity pulls the solution through the membrane. Next, a solution of avidin-HRP is poured over the membrane, rinsed, and then the detecting solution (HRP substrate) is poured over the membrane. SAM concentration is then estimated by determining the intensity of the blue color on the membrane.

All patents, patent applications and journal publications cited in this application including all cited references in those applications, are hereby incorporated by reference in their entirety for all purposes to the same extent as if each individual patent, patent application or publication were so individually denoted.

While the many embodiments of the invention have been disclosed above and include presently preferred embodiments, many other embodiments and variations are possible within the scope of the present disclosure and in the appended claims that follow. Accordingly, the details of the preferred embodiments and examples provided are not to be construed as limiting. It is to be understood that the terms used herein are merely descriptive rather than limiting and that various changes, numerous equivalents may be made without departing from the spirit or scope of the claimed invention.

What is claimed is:

1. An antibody specifically recognizing S-adenosyl-xnethionine (SAM) said antibody having a cross reactivity with S-adenosylhomnocysteine (SAH) and analogs thereof of less than 10% and wherein said antibody is prepared by inoculating a host animal with an immunogen comprising an immunogenic substance directly or indirectly coupled to a S-adenosylmethionine hapten of the formula:

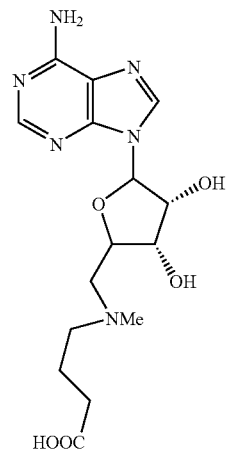 [SMILES: CN(CCCC(=O)O)CC1OC(n2cnc3c(N)ncnc32)[C@H](O)[C@@H]1O]

its enantiomers, diastereomers, enantiomerically enriched mixtures, racemic mixtures thereof, isotopically enriched forms thereof, crystalline forms, non-crystalline forms, amorphous forms thereof, charged and non-charged forms thereof, solvates thereof, metabolites thereof, or salts thereof.

2. The antibody of claim 1, having a cross reactivity with SAH and analogs thereof of less than 5%.

3. The antibody of claim 1, having a cross reactivity with SAH and analogs thereof of less than 3%.

4. The antibody of claim 1, conjugated directly, indirectly via a spacer or linker of 2-10 atoms in length to a detectable label or complexed to a detectable label via a binding pair such as avidin/streptavidin and biotin.

5. The conjugate or complex of claim 4 wherein the detectable label is selected from the group consisting of an enzyme label, a radioactive label, a chromogenic label, a fluorescent label, a phosphorescent label, a chemiluminescent label, a bioluminescent label, gold sol, and a particulate label.

6. The conjugate or complex of claim 5 wherein the detectable label is an enzyme label.

7. An antibody which selectively binds to SAM and analogs of SAM said antibody paving a cross reactivity with S-adenosylhomocysteine (SAH) and analogs thereof of less than 10% and wherein said antibody is prepared by inoculating a host animal with an immunogen comprising an immunogenic substance directly or indirectly coupled to a S-adenosylmethionine hapten of the formula:

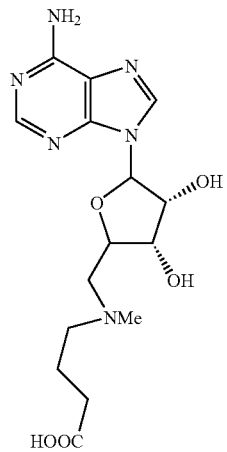 [SMILES: CN(CCCC(=O)O)CC1OC(n2cnc3c(N)ncnc32)[C@H](O)[C@@H]1O]

its enantiomers, diastereomers, enantiomerically enriched mixtures, racemic mixtures thereof, isotopically enriched forms thereof, crystalline forms, non-crystalline forms, amorphous forms thereof, charged and non-charged forms thereof, solvates thereof, metabolites thereof, or salts thereof.

8. The antibody of claim 7, wherein said antibody is a monoclonal antibody.

9. The antibody of claim 7, wherein said antibody is a polyclonal antibody, derived from mice, rats, rabbits, goats, sheep, or chicken.

10. A conjugate comprising the antibody of claim 7 conjugated directly or indirectly to a detectable label.

11. The conjugate of claim 10 wherein the detectable label is selected from the group consisting of an enzyme label, a radioactive label, a chromogenic label, a fluorescent label, a phosphorescent label, a chemiluminescent label, a bioluminescent label, gold sol, and a particulate label.

12. The conjugate of claim 11 wherein the detectable label is an enzyme label.

13. An antibody useful in an immunoassay to detect or measure S-adenosylmethionine in a sample, wherein said antibody specifically binds to S-adenosylmethionine and wherein said antibody has a cross reactivity with S-adenosylhomocysteine (SAH) and analogs thereof of less than 10% and wherein said antibody is prepared by inoculating a host animal with an immunogen comprising an immunogenic substance directly or indirectly coupled to a S-adenosylmethionine hapten of the formula:

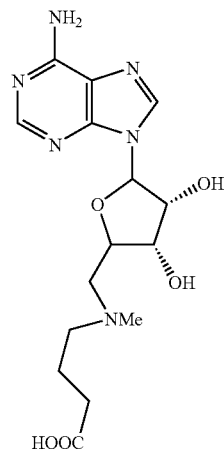

its enantiomers, diastereomers, enantiomerically enriched mixtures, racemic mixtures thereof, isotopically enriched forms thereof, crystalline forms, non-crystalline forms, amorphous forms thereof, charged and non-charged forms thereof, solvates thereof metabolites thereof, or salts thereof.

14. A conjugate comprising the antibody of claim 13 conjugated directly or indirectly to a detectable label.

15. The conjugate of claim 14 wherein the detectable label is selected from the group consisting of an enzyme label, a radioactive label, a chromogenic label, a fluorescent label, a phosphorescent label, a chemiluminescent label, a bioluminescent label, gold sol, and a particulate label.

16. The conjugate of claim 15 wherein the detectable label is an enzyme label.

* * * * *